(12) United States Patent
Mayou et al.

(10) Patent No.: US 7,793,545 B2
(45) Date of Patent: Sep. 14, 2010

(54) AUDIOMETER WITH INTERCHANGEABLE TRANSDUCER

(75) Inventors: David P. Mayou, Minneapolis, MN (US); Michael R. Burr, Minneapolis, MN (US)

(73) Assignee: Benson Medical Instruments Company, Minneapolis, MN (US)

( * ) Notice: Subject to any disclaimer, the term of this patent is extended or adjusted under 35 U.S.C. 154(b) by 356 days.

(21) Appl. No.: 11/867,498

(22) Filed: Oct. 4, 2007

(65) Prior Publication Data

US 2009/0090165 A1    Apr. 9, 2009

(51) Int. Cl.
 *A61B 5/12* (2006.01)
(52) U.S. Cl. ............... 73/585; 73/1.82; 600/559; 702/57
(58) Field of Classification Search .......... 73/585, 73/1.82; 600/559; 381/23.1, 58, 60, 312, 381/314, 323; 702/57
See application file for complete search history.

(56) References Cited

U.S. PATENT DOCUMENTS

| | | | | |
|---|---|---|---|---|
| 2,511,482 | A | * | 6/1950 | Shaper .............. 73/585 |
| 3,392,241 | A | | 7/1968 | Weiss et al. |
| 3,745,674 | A | | 7/1973 | Thompson et al. |
| 3,793,485 | A | | 2/1974 | Feezor et al. |
| 3,808,354 | A | | 4/1974 | Feezor et al. |
| 3,809,811 | A | | 5/1974 | Delisle et al. |
| 3,905,131 | A | | 9/1975 | Feezor et al. |
| 3,974,335 | A | | 8/1976 | Blackledge |
| 3,977,394 | A | | 8/1976 | Jones et al. |
| 4,022,975 | A | | 5/1977 | Krass |
| 4,024,499 | A | | 5/1977 | Bosscher |
| 4,038,496 | A | | 7/1977 | Feezor |
| 4,107,465 | A | | 8/1978 | Charlebois et al. |
| 4,157,456 | A | | 6/1979 | Voss |
| 4,224,468 | A | | 9/1980 | Calder, Jr. |
| 4,275,744 | A | | 6/1981 | Thornton et al. |

(Continued)

FOREIGN PATENT DOCUMENTS

JP    6175817    6/1994

(Continued)

OTHER PUBLICATIONS

Electronic File Wrapper of U.S. Appl. No. 11/897,216.

(Continued)

*Primary Examiner*—J M Saint Surin
(74) *Attorney, Agent, or Firm*—Patterson Thuente Christensen Pedersen, P.A.

(57) ABSTRACT

An audiometer including a processor controlled test signal generator is adjustable so as to produce a uniform output signal when coupled with a transducer load. Each transducer set to be used with the test signal generator includes recordable indicia in written or electronic form, upon which correction values for adjusting the electronic signal output of the audiometer module to produce a desired sound output from the each transducer in the transducer set. When the transducer set is connected to the audiometer module, the correction values are either retrieved automatically from the electronic indicia, which may be an EEPROM, or are input to the processor manually by a user through an interface such as a keyboard. These correction values are then used by the processor to dynamically adjust the output of the audiometer to correct for sound output response deviation of each transducer in the transducer set.

20 Claims, 37 Drawing Sheets

U.S. PATENT DOCUMENTS

| | | |
|---|---|---|
| 4,284,847 A | 8/1981 | Besserman |
| 4,321,427 A | 3/1982 | Singh |
| 4,476,724 A | 10/1984 | Gotze |
| 4,489,610 A | 12/1984 | Slavin |
| 4,548,082 A | 10/1985 | Engebretson et al. |
| 4,615,007 A | 9/1986 | King et al. |
| 4,667,683 A | 5/1987 | Dugot |
| 4,731,850 A | 3/1988 | Levitt et al. |
| 4,764,957 A | 8/1988 | Angelini et al. |
| 4,768,165 A * | 8/1988 | Hohn ........................ 73/585 |
| 4,847,763 A | 7/1989 | Moser et al. |
| 4,862,505 A | 8/1989 | Keith et al. |
| 4,933,873 A | 6/1990 | Kaufman et al. |
| 4,964,304 A | 10/1990 | Eckstein |
| 5,023,783 A | 6/1991 | Cohen et al. |
| 5,111,506 A | 5/1992 | Charpentier et al. |
| 5,119,826 A | 6/1992 | Baart de la Faille |
| 5,197,332 A | 3/1993 | Shennib |
| 5,239,872 A | 8/1993 | Meyer-Bisch |
| 5,282,475 A | 2/1994 | Urbach et al. |
| 5,303,327 A | 4/1994 | Sturner et al. |
| 5,363,859 A | 11/1994 | Tuckett et al. |
| RE34,961 E | 6/1995 | Widin et al. |
| 5,428,998 A | 7/1995 | Downs |
| 5,511,982 A | 4/1996 | Pigache et al. |
| 5,525,977 A | 6/1996 | Suman |
| 5,562,104 A | 10/1996 | Hochberg et al. |
| 5,645,074 A | 7/1997 | Shennib et al. |
| 5,737,389 A | 4/1998 | Allen |
| 5,811,681 A | 9/1998 | Braun et al. |
| 6,118,877 A | 9/2000 | Lindemann et al. |
| 6,366,863 B1 | 4/2002 | Bye et al. |
| 6,396,930 B1 * | 5/2002 | Vaudrey et al. ............. 381/60 |
| 6,416,482 B1 * | 7/2002 | Braun et al. ............... 600/559 |
| 6,468,224 B1 | 10/2002 | Foreman et al. |
| 6,496,585 B1 | 12/2002 | Margolis |
| 6,644,120 B1 | 11/2003 | Braun et al. |
| 7,210,353 B2 | 5/2007 | Braun et al. |
| 2003/0065276 A1 * | 4/2003 | Akita ......................... 600/559 |
| 2008/0167575 A1 * | 7/2008 | Cronin et al. .............. 600/559 |
| 2008/0269636 A1 * | 10/2008 | Burrows et al. ............ 600/559 |
| 2009/0063080 A1 | 3/2009 | Foreman |
| 2009/0323989 A1 * | 12/2009 | Capper et al. .............. 381/151 |

FOREIGN PATENT DOCUMENTS

| | | |
|---|---|---|
| JP | 7308310 | 11/1995 |

OTHER PUBLICATIONS

Bernafon, Inc.'s Rebuttal Claim Construction Memorandum for U.S. Patent No. 5,811,681, Civil Action No. 02-77CV (JNE/JGL), 12 Pgs.

Rion Co., Ltd., *AA-75 Audiometer Operation Manual*, Excerpt from: Operation Manual, pp. 10, (including English translation), Japan, No. 22920 95-10 ()ct. 1995), 10 Pgs.

Virtual Corporation, *Virtual Model 320 Clinical Audiometer User Manual*, 1988, 148 Pgs.

Benson Medical Instruments Company, *Computer Controlled Audiometer (Model CCA100)*, Document Version #1.30, Dec. 13, 1994, 45 Pgs.

Benson Medical Instruments Company, *Controlled Audiometer (Model CCA100)*, Document Version #1.20, Nov. 15, 1993, 14 Pgs.

Benson Medical Instruments Company, *CCA-100 Operating Manual*, V. 1.10, 1996, 47 Pgs.

Benson Medical Instruments Company, *System 100 Operating Manual*, V. 0.96, 1995, 46 Pgs.

Maico, *Service Manual MA 728 and MA 728M*, 41 Pgs.

Maico, *Operating Instructions Maico 728M Automatic Computer Audiometer—with Maico Warranty Registration*, 33 Pgs.

Tremetrics Medical Instruments, *Sales Meeting, Technical Data and Troubleshooting*, Nov. 1990, 35 Pgs.

Tracor Instruments Austin, Inc. *RA600 Microprocessor Group Audiometer. Service Manual*, Jun. 1985, 37 Pgs.

RA 400 Microprocessor Audiometer; Operation Manual 78835A; Sep. 1983; Tracor Instruments; 46 Pgs.

USAEHA; Hearing Evaluation Automated Registry System (HEARS)—USAEHA Technical Guide No. 167A; Audiometer Operation Manual; Feb. 1991; Includes Appendix A. 200 Pgs.

Benson Medical Instruments Company, *System 100 Professional*, 2 Pgs.

Benson Medical Instruments Company, *Price List Jan. 3, 1996*, 1 Pg.

Adnan Shennib, MS et al., "Personal Digital Audiometry: A New Dimension in Testing", *Hearing Instruments*, vol. 45, No. 3, Mar. 1994, 3 Pgs.

Decibel Instruments, Inc., Instrument Manual, ProDigit™ 2000 Personal Digital Audiometer™, Version A1.1, Copyright © 1995, 46 Pgs.

Clinical Audiometry for Windows™, Version A1.4, by Decibel Instruments, Inc., User's Manual ProDigit™ 2000 Personal Digital Audiometer™, Copyright © 1995, 87 Pgs.

Decibel, "Introducing Clinical Audiometry for Windows from Decibel Instruments, Inc.," 1995, 1 Pg.

Decibel, "Introducing Screening Audiometry for Windows from Decibel Instruments, Inc.," 1995, 1 Pg.

* cited by examiner

AUDIOMETER WITH INTERCHANGEABLE TRANSDUCER

FIELD OF THE INVENTION

The instant invention relates to audiometers and more specifically to calibration of audiometers and associated components.

COMPUTER PROGRAM LISTING APPENDIX

A computer program listing is included herewith as Appendix A to this application, the computer program listing consisting of ASCII text files submitted electronically herewith via the USPTO EFS-Web system. Appendix A includes the following files:

| TITLE | SIZE IN BYTES | DATE OF CREATION |
|---|---|---|
| AppendixA.txt | 9,885 | Dec. 04, 2007 |

The entire contents of Appendix A, including without limitation, the aforementioned files, is hereby incorporated herein by reference.

BACKGROUND OF THE INVENTION

Audiometers for testing the hearing of human subjects have been in widespread use for many years. Typically, an audiometer includes a test signal generator component for generating audio signals, and one or more transducers for converting the signals to audible sound in the form of test tones or speech. The test signal generator is often controlled by a computer or microprocessor so as to enable audio testing of subjects to take place automatically without a highly trained operator in attendance.

Test sounds are typically presented to the test subjects at precise absolute sound pressure levels for accuracy, standardization, and comparison purposes. Due to variability in component values and characteristics, however, test signal generators may output significantly different output levels and different transducers may produce significantly different absolute sound pressure levels when supplied with an electrical signal of a uniform value. For these reasons, the test signal generator and transducers of prior art audiometers are calibrated together. That is, the test signal generator is matched to a single transducer set and adjusted to give the desired absolute sound pressure levels. An example of such a prior art audiometer apparatus is disclosed in U.S. Pat. No. 6,468,224 to Foreman, hereby fully incorporated herein by reference.

A drawback of these prior art audiometer systems arises when transducers are lost or damaged. The test signal generator and the specific transducers that are to be used with the test signal generator in these prior systems must have been at least once physically connected with each other and adjusted to ensure the accuracy of the sound pressure levels output by the transducers. Consequently, if the transducer is lost or damaged, a new transducer must be matched and re-calibrated with the test signal generator. This typically either involves shipping the audiometer to the original manufacturer or authorized repair location to enable the recalibration and then returning the newly calibrated audiometer to the service location or requires an on-site visit by a skilled repair technician with the proper equipment. Attempts have been made to address this problem by including a limited number of spare transducers, and providing the audiometer with multiple tables of correction values stored therein that can be switched automatically or manually when a spare transducer is substituted. This, however, is not a completely satisfactory solution since the transducers and test signal generator must still have been once physically connected. Also, once supply of spare transducers is depleted, new transducers need to be matched by recalibration on site or at a repair facility. For the user, if a backup audiometer with calibrated transducer is not available, the result is extended downtime when the audiometer is not available for use. Moreover, it is often not economically feasible to maintain backups because of the relatively high cost of precision automatic audiometers.

What is still needed in the industry is an audiometer system that enables any transducer to be used with the test signal generator without having been specifically matched.

SUMMARY OF THE INVENTION

The present invention addresses the needs of the industry for an audiometer system that enables any transducer to be used with the test signal generator without having been specifically matched. In an embodiment of the invention, an audiometer module including a processor controlled test signal generator is adjustable so as to produce a uniform output signal when coupled with a transducer load. Each transducer set to be used with the test signal generator includes recordable indicia in written or electronic form, upon which are recorded correction value for adjusting the electronic signal output of the audiometer module to produce a desired sound output from the each transducer in the transducer set. When the transducer set is connected to the audiometer module, the correction values are either retrieved automatically from the electronic indicia, which may be an EEPROM, or are input to the processor manually by a user through an interface such as a keyboard. These correction values are then used by the processor to dynamically adjust the output of the audiometer to correct for sound output response deviation of each transducer in the transducer set.

According to an embodiment of the invention, an audiometer for testing the hearing of a test subject includes an audiometer module with a test signal generator and a processor with associated memory and control logic operably coupled to the test signal generator. The processor controls the test signal generator to generate an electronic test signal having a first signal magnitude, and further controls the test signal generator to adjust the first signal magnitude to a second signal magnitude in proportion to a transducer correction value and deliver the electronic test signal with the second signal magnitude at an output of the audiometer module. A transducer is communicatively coupled to the output of the audiometer module, wherein the transducer generates a sound signal having a desired magnitude when the electronic test signal having the second signal magnitude is delivered to the transducer. The transducer further comprises a data storage structure with the transducer correction value is stored therein. The audiometer further includes an interface selectively couplable with the processor for delivering the transducer correction factor to the processor.

In embodiments of the invention the data storage structure may be electronic memory such as an EEPROM. In other embodiments, the data storage structure may be printed indicia attached to the transducer. The interface may include a keyboard communicatively coupled directly to the processor or to a personal computer communicatively coupled to the processor. In embodiments where the data storage structure is electronic memory, the interface may include a one-wire interface controller.

Embodiments of the invention may also include a method for calibrating an audiometer and a transducer. The audiometer includes a test signal generator and a processor, wherein the processor controls the test signal generator to generate a plurality of electronic test signals each having a first signal magnitude. The processor further controls the test signal generator to adjust the first signal magnitude of each test signal to a second signal magnitude in proportion to a corresponding transducer correction value and to deliver the test signals to an input of the transducer at the second signal magnitude. The method includes applying each one of a plurality of input signals to the input of the transducer, each of the input signals having a signal frequency corresponding to a signal frequency of one of the test signals, and determining a target signal magnitude for each of the plurality of input signals that results in a desired magnitude of sound output from the transducer. For each of the plurality of input signals, a transducer correction value is determined for the audiometer that results in the corresponding test signal having a second signal magnitude equal to the target signal magnitude determined for the input signal. The transducer correction values are then stored in a data storage structure associated with the transducer. The stored transducer correction values are then delivered to the audiometer to be used to correct for transducer response deviation.

Other embodiments may include a method of calibrating an audiometer and transducer, the audiometer comprising a test signal generator and a processor controlling the test signal generator. The method includes storing a plurality of transducer correction values in a data storage structure associated with the transducer, retrieving the transducer correction values from the transducer using a controller associated with the audiometer and delivering the retrieved transducer correction values to the processor. When a test signal is generated with the test signal generator, the processor is used to adjust a magnitude of the test signal according to at least one of the transducer correction values. The step of storing the plurality of correction values in a data storage structure associated with the transducer may include writing the correction values to an EEPROM or inscribing the correction values on a label or tag.

An advantage of certain embodiments of the invention is that any transducer set with which correction values have been associated may be used with an audiometer module without the need for recalibration by a technician. Furthermore, different types of transducers, such as bone vibrators, sound field speakers, and insert phones may be used and interchanged without calibration.

The present invention enables a tester to have a fully calibrated system, even if the transducers and test signal generator have never been previously connected. The user may receive a set of transducers with associated correction values, and have a fully calibrated system, even though the components have never been together.

BRIEF DESCRIPTION OF THE DRAWINGS

The invention may be more completely understood in consideration of the following detailed description of various embodiments of the invention in connection with the accompanying drawings, in which.

Figure 1:
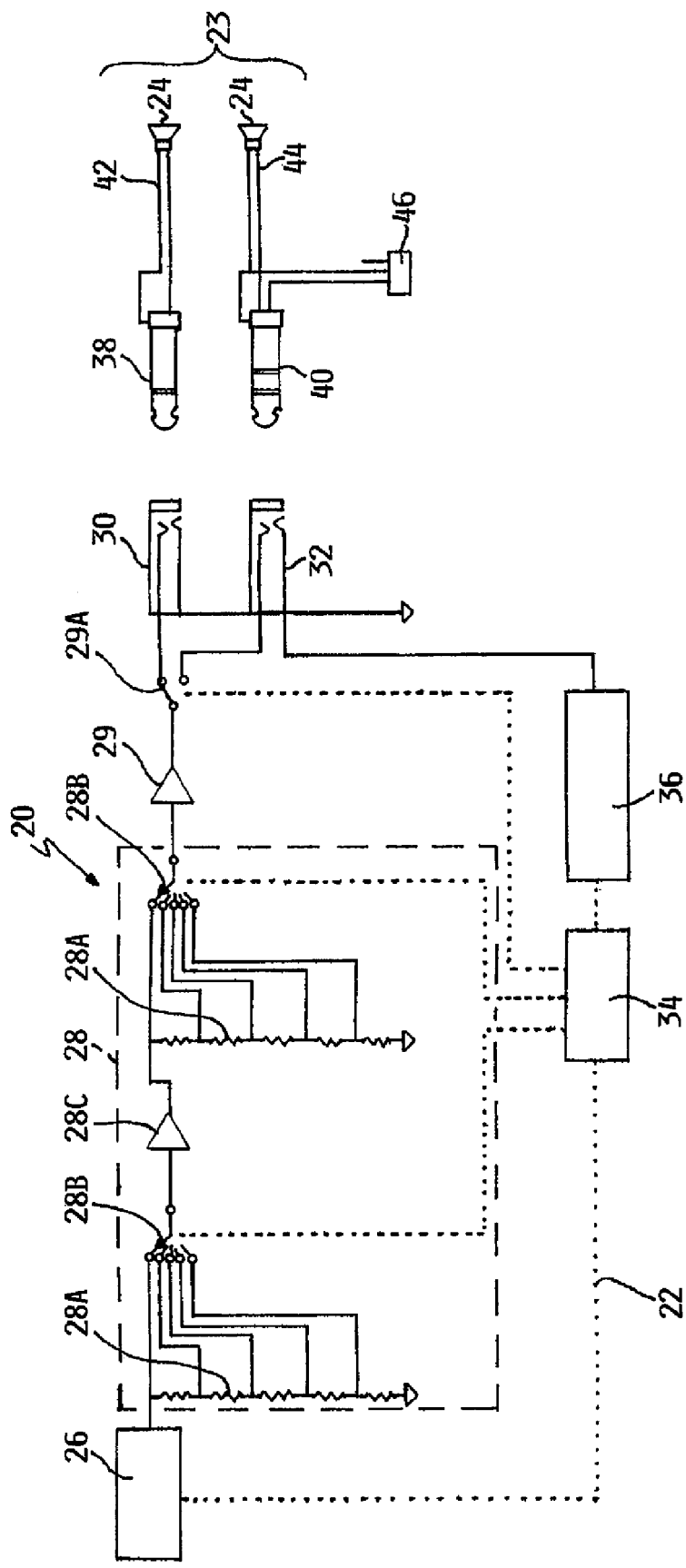
FIG. 1 is a schematic diagram of an embodiment of a computer controlled audiometer with interchangeable transducer.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

As depicted in the schematic diagram of FIG. 1, an embodiment of a computer controlled audiometer with interchangeable transducer system 20 generally includes an audiometer module 22 and a transducer set 23 including one or more transducers 24. Audiometer module 22 generally includes an oscillator 26, variable attenuator 28, final amplifier 29, channel selector switch 29A, a left signal output 30, a right signal output 32, a central processing unit (CPU) module 34, and a one-wire interface controller 36. Transducer set 23 generally includes left and right input jacks 38, 40, transducers 24 coupled thereto with wires 42, 44, and a non-volatile memory chip 46. Variable attenuator 28 generally includes a plurality of resistor networks 28A, a plurality of magnitude selector switches 28B, and one or more amplifiers 28C.

In a particular embodiment, a known CCA-100e Computer Controlled Audiometer, available from Benson Medical Instruments of Minneapolis, MN, may be modified to include the system of the present invention. Oscillator 26, attenuator 28, CPU module 34, left and signal outputs 30, 32, as well as ancillary components power supply 50, and CPU I/O section 52 are depicted for the example embodiment in block schematic diagram form in FIGS. 2A-2D, and in detailed schematic form in FIGS. 3A-3J and 7A-7E.

Figure 1A:
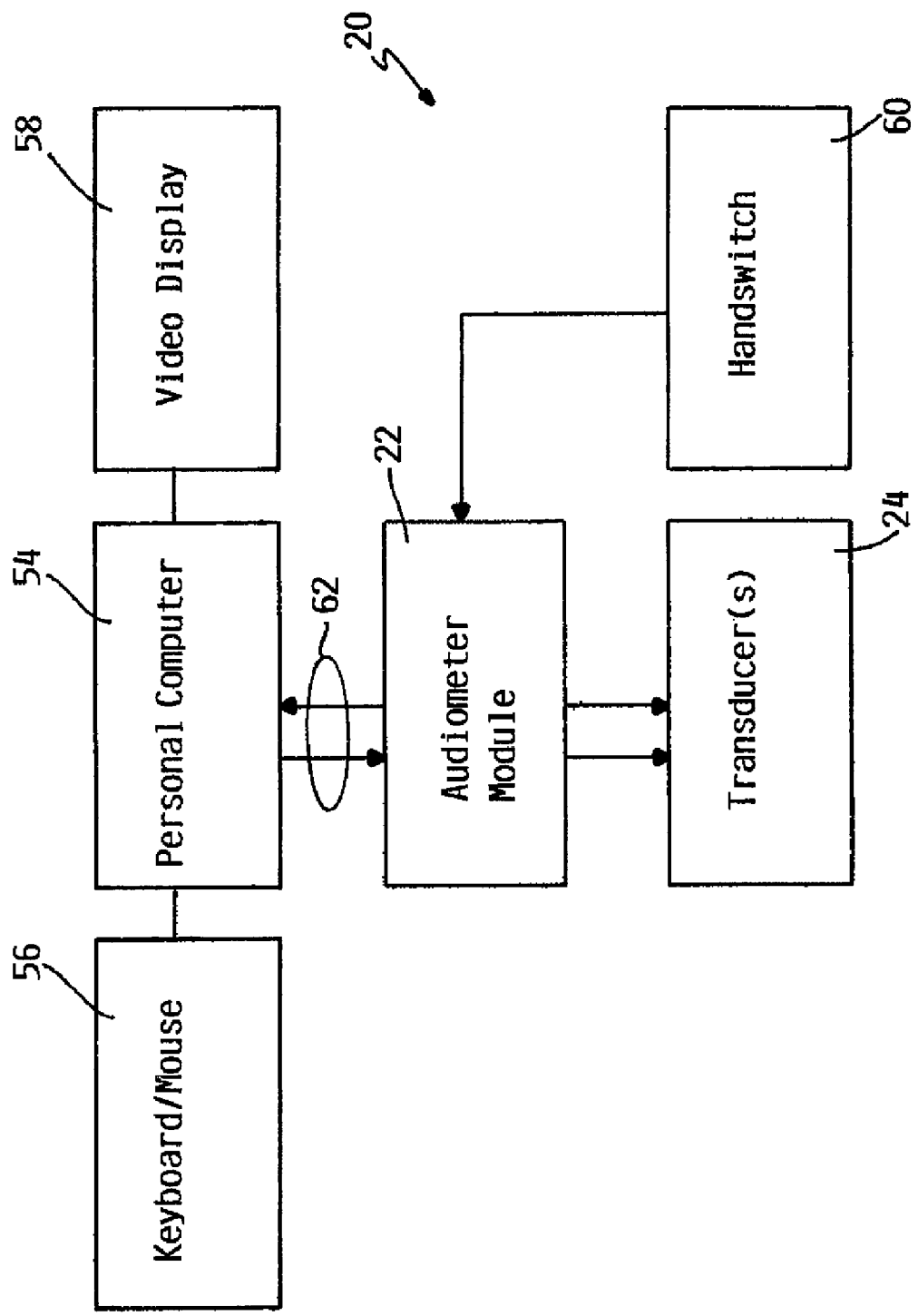
FIG. 1A is a block diagram of a computer controlled audiometer with personal computer interface.
Figure 2A:
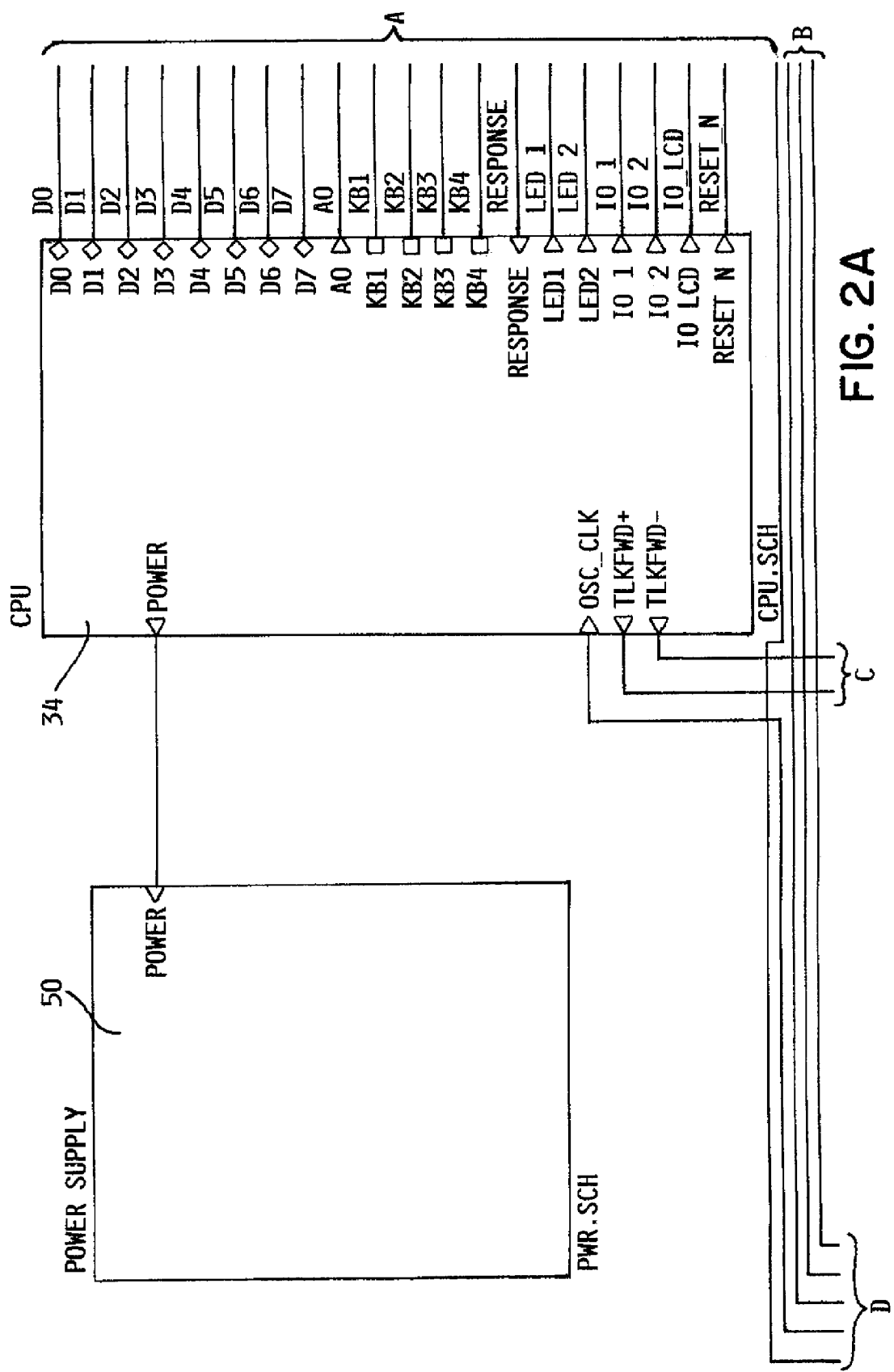
FIGS. 2A-2D are each a portion of a block diagram of a computer controlled audiometer embodying the present invention.
Figure 2B:
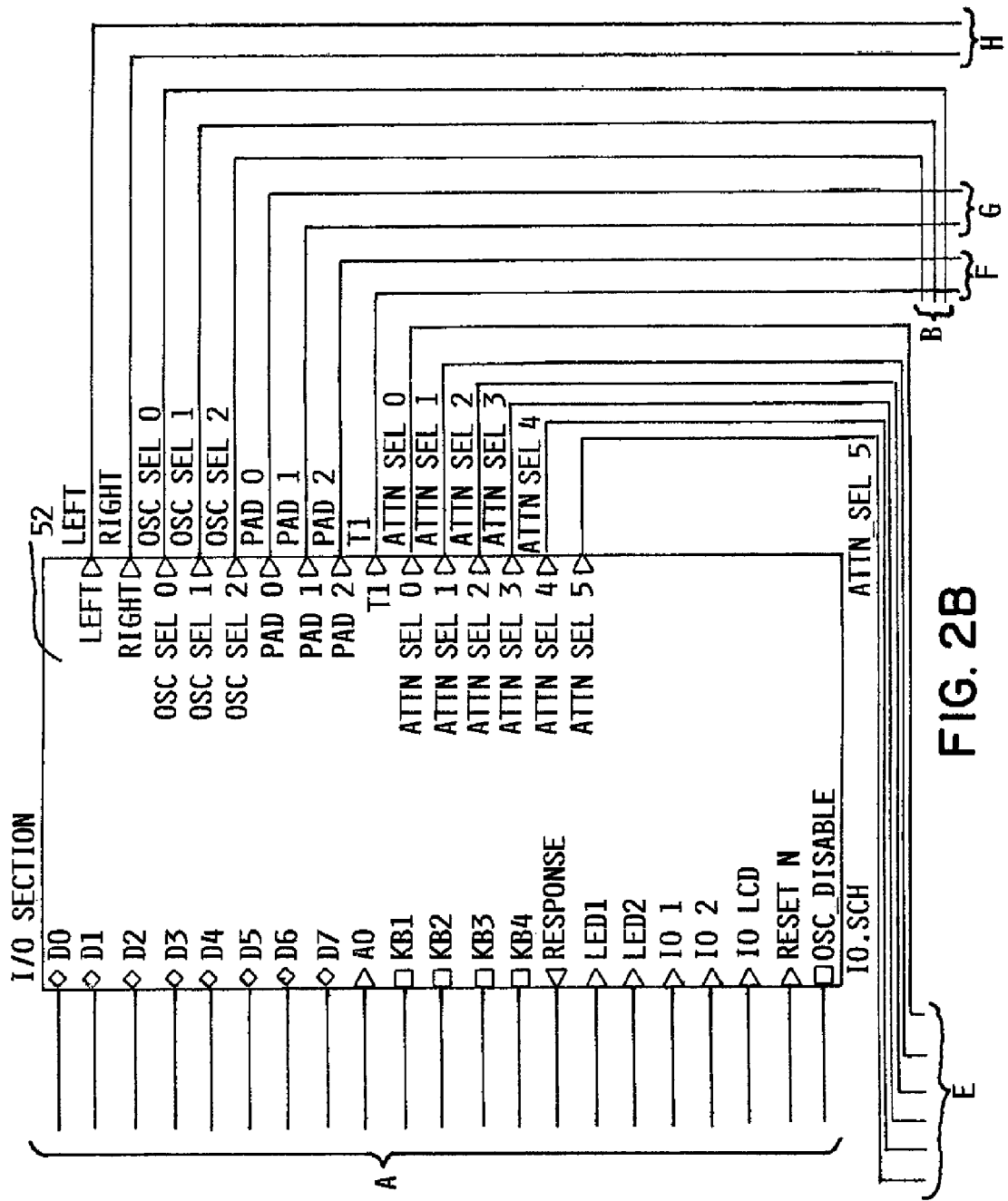
Figure 2C:
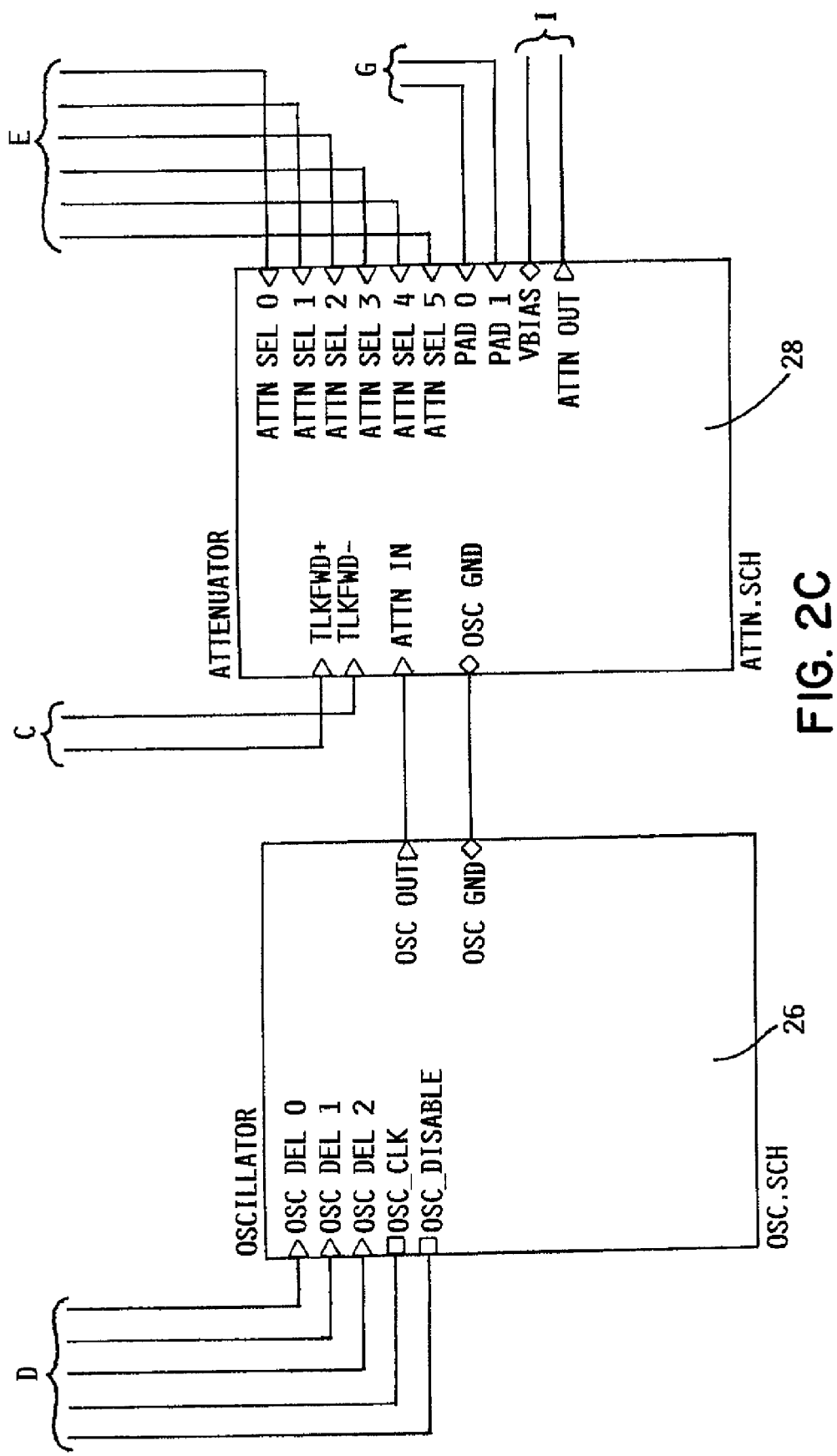
Figure 2D:
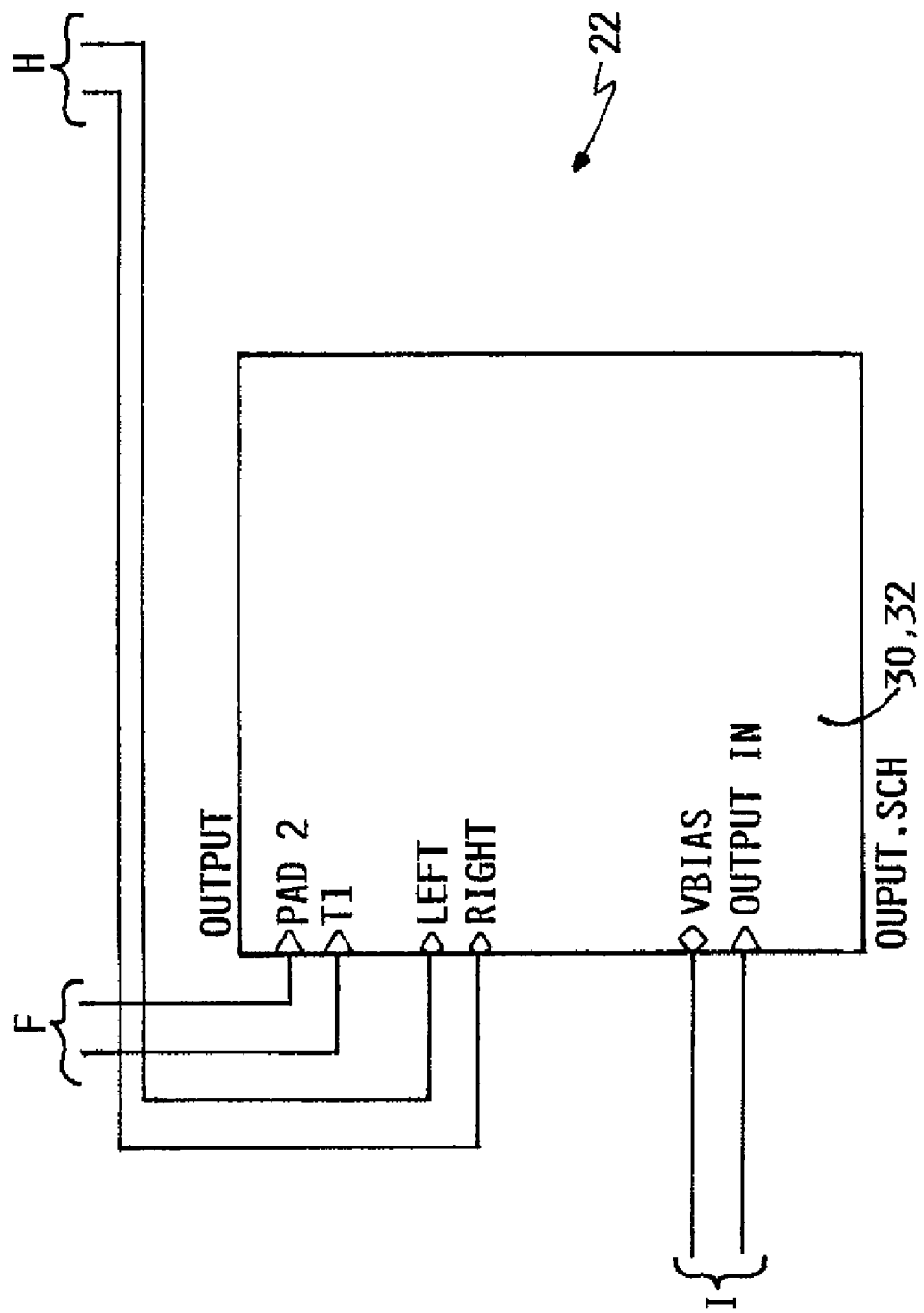
Figure 3A:
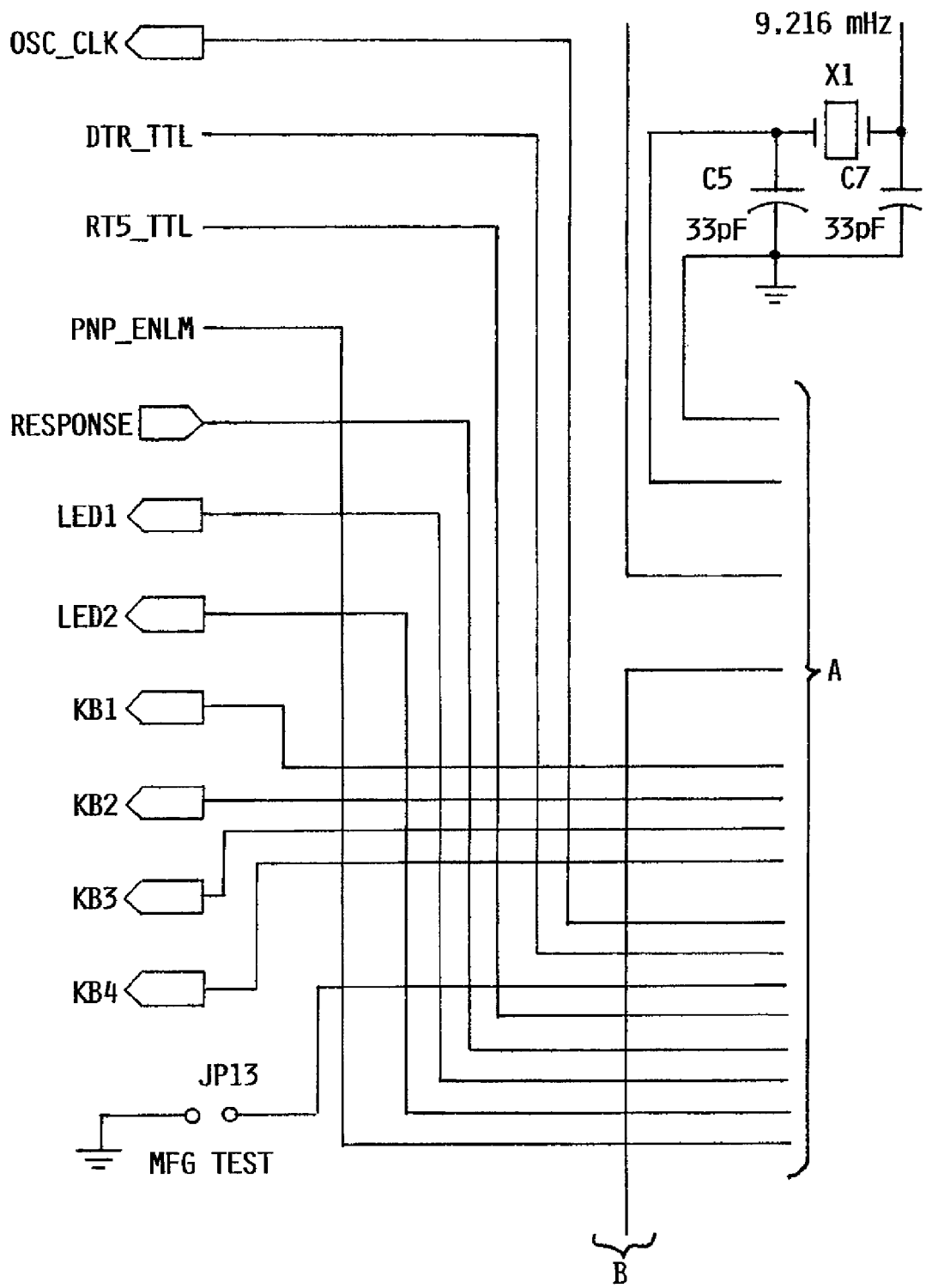
FIGS. 3A-3J are each a portion of a schematic circuit diagram of a central processing unit module (CPU) of the audiometer of FIG. 2.
Figure 3B:
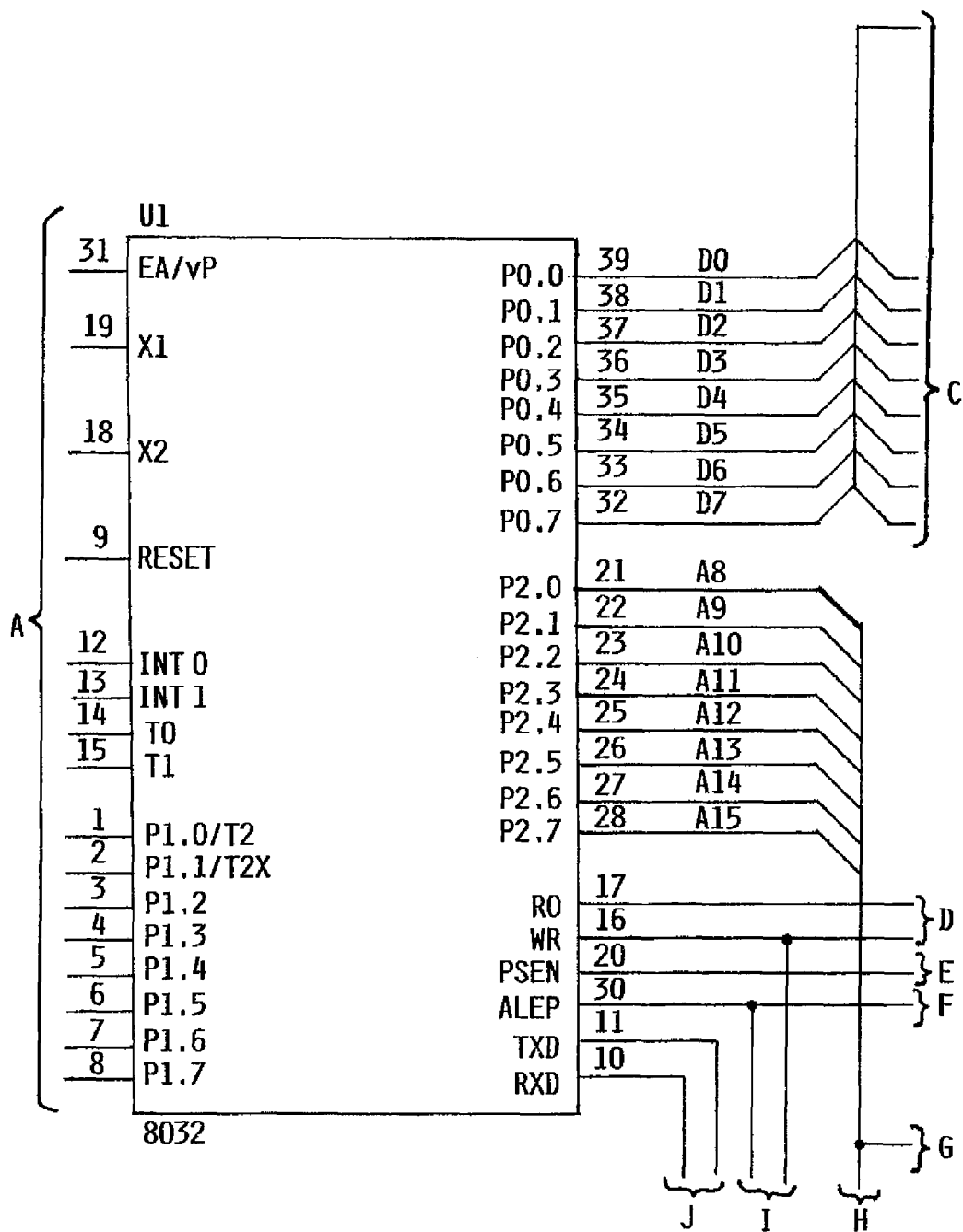
Figure 3C:
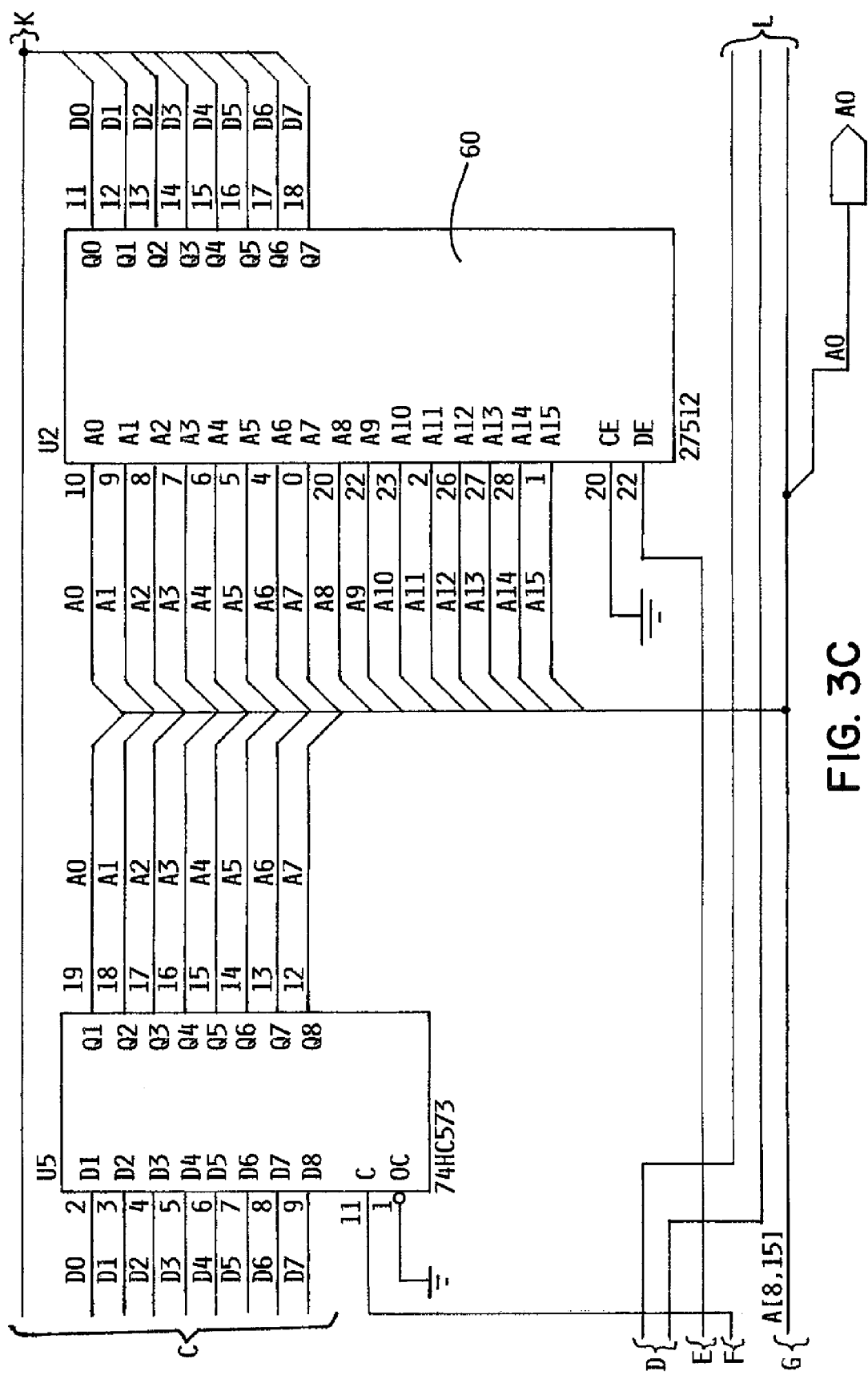
Figure 3D:
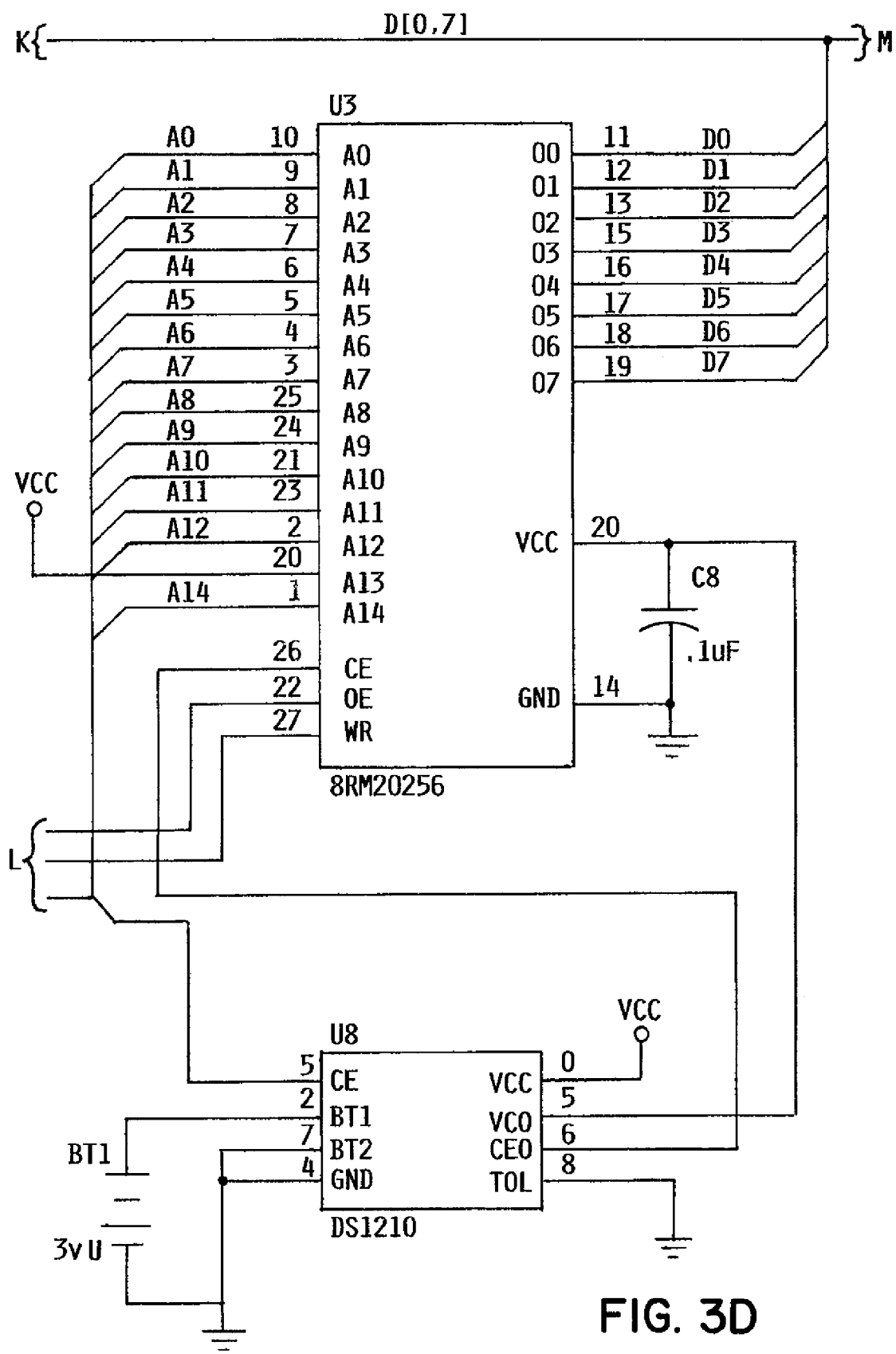
Figure 3E:
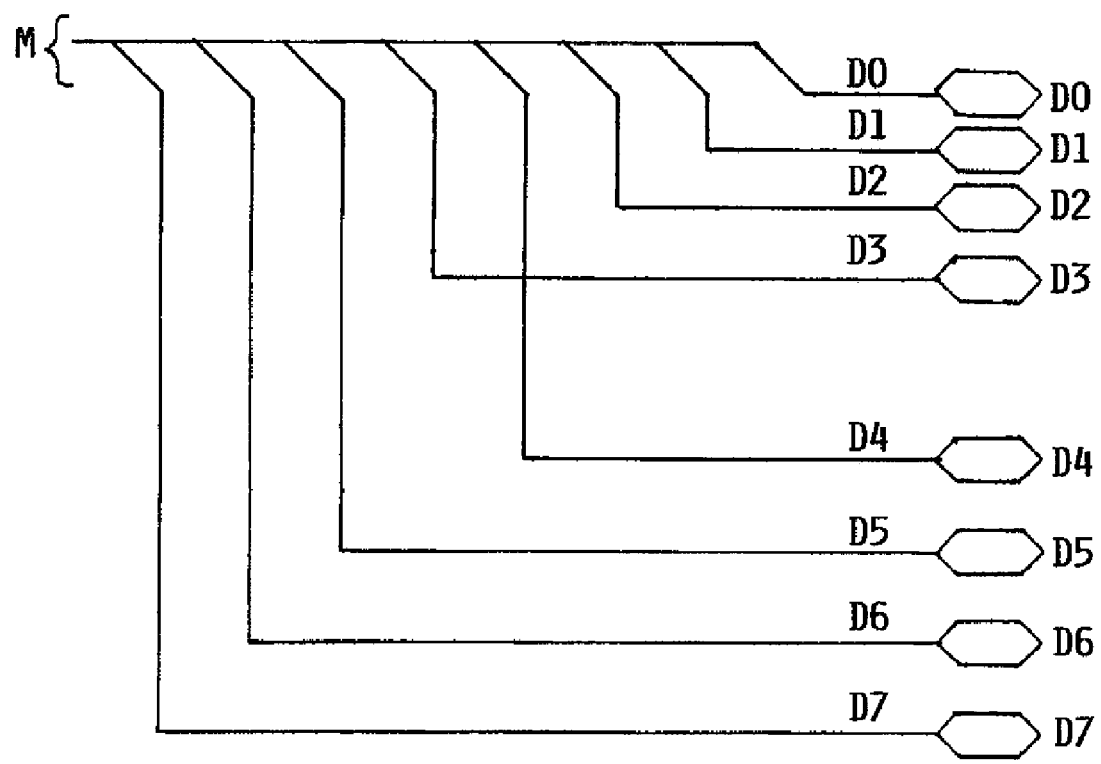
Figure 3F:
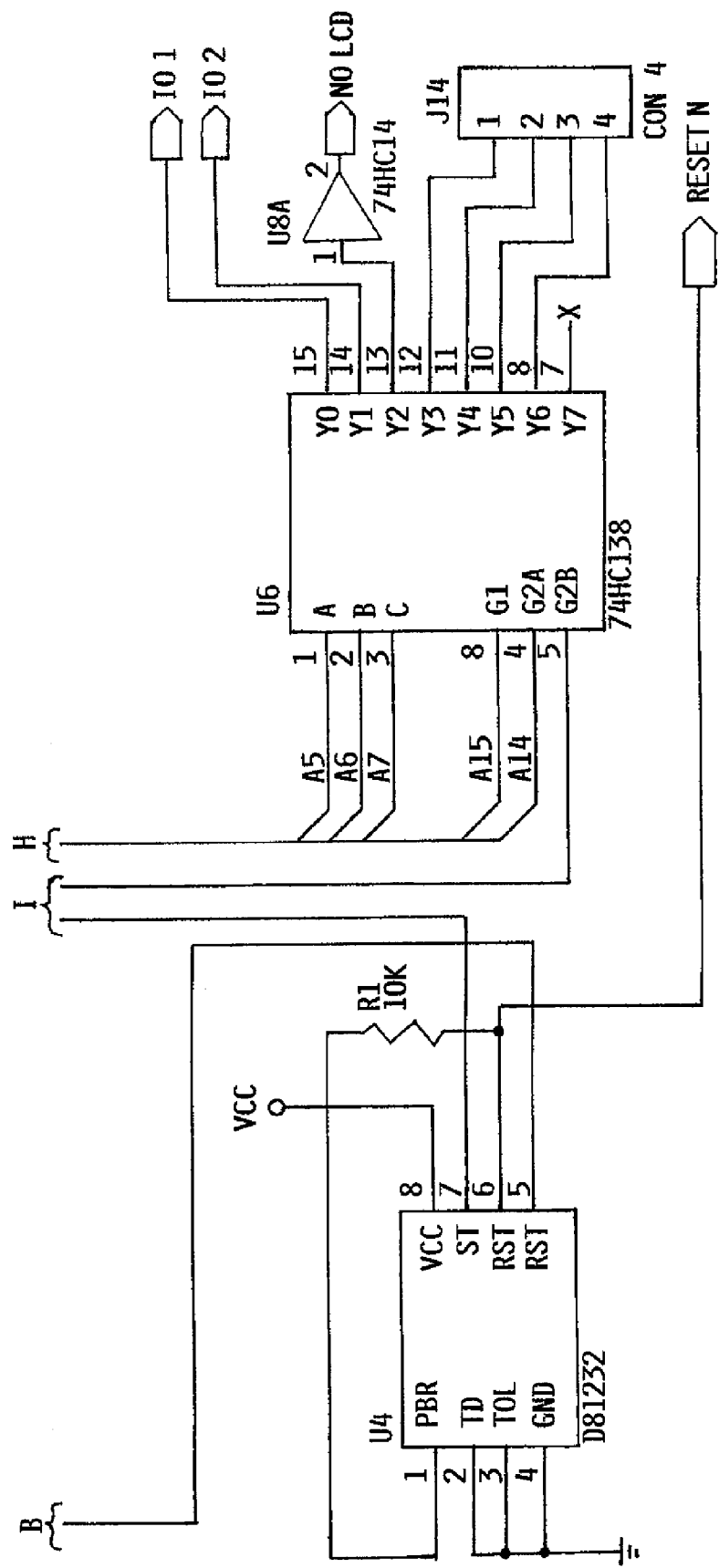
Figure 3G:
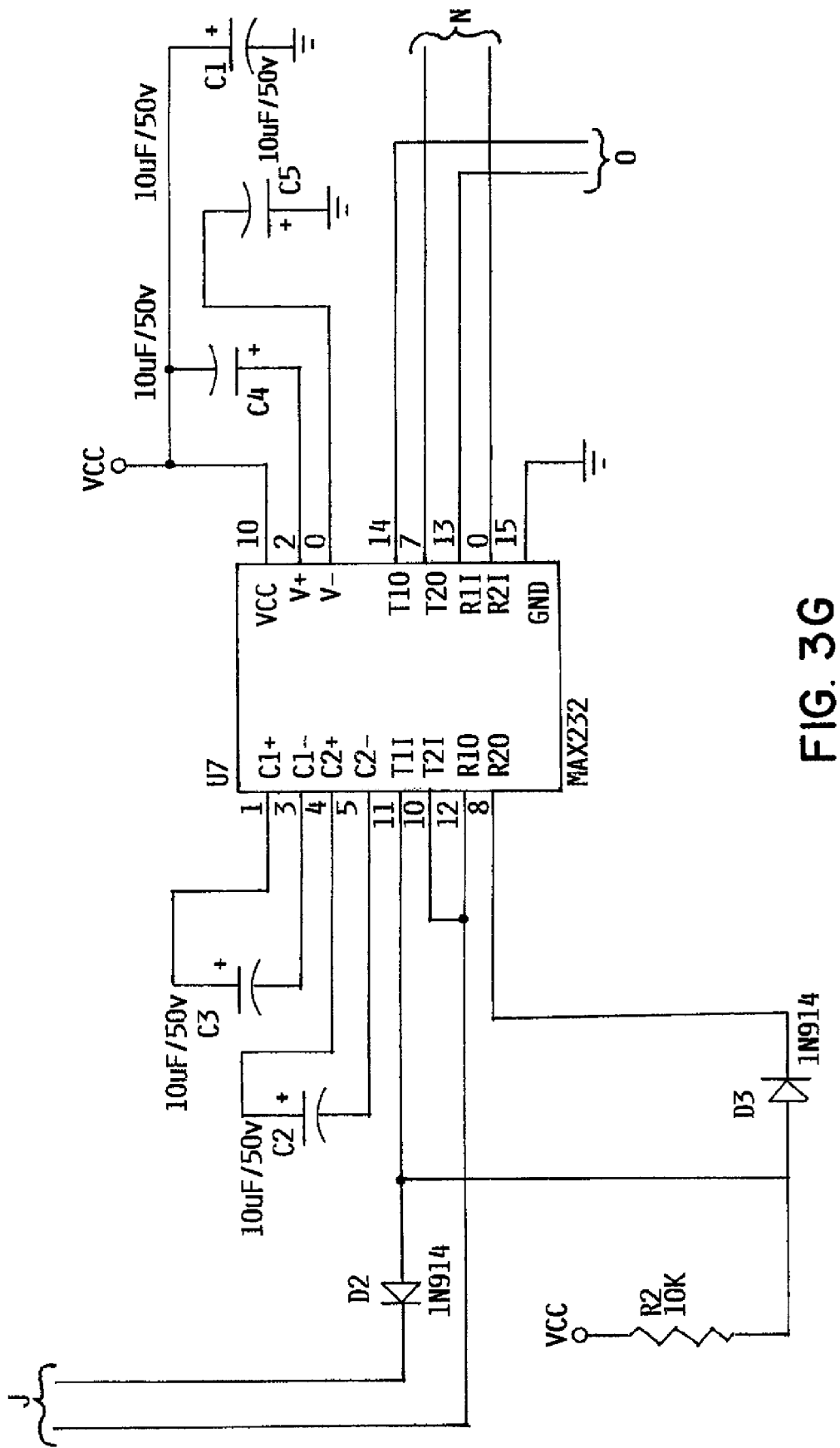
Figure 3H:
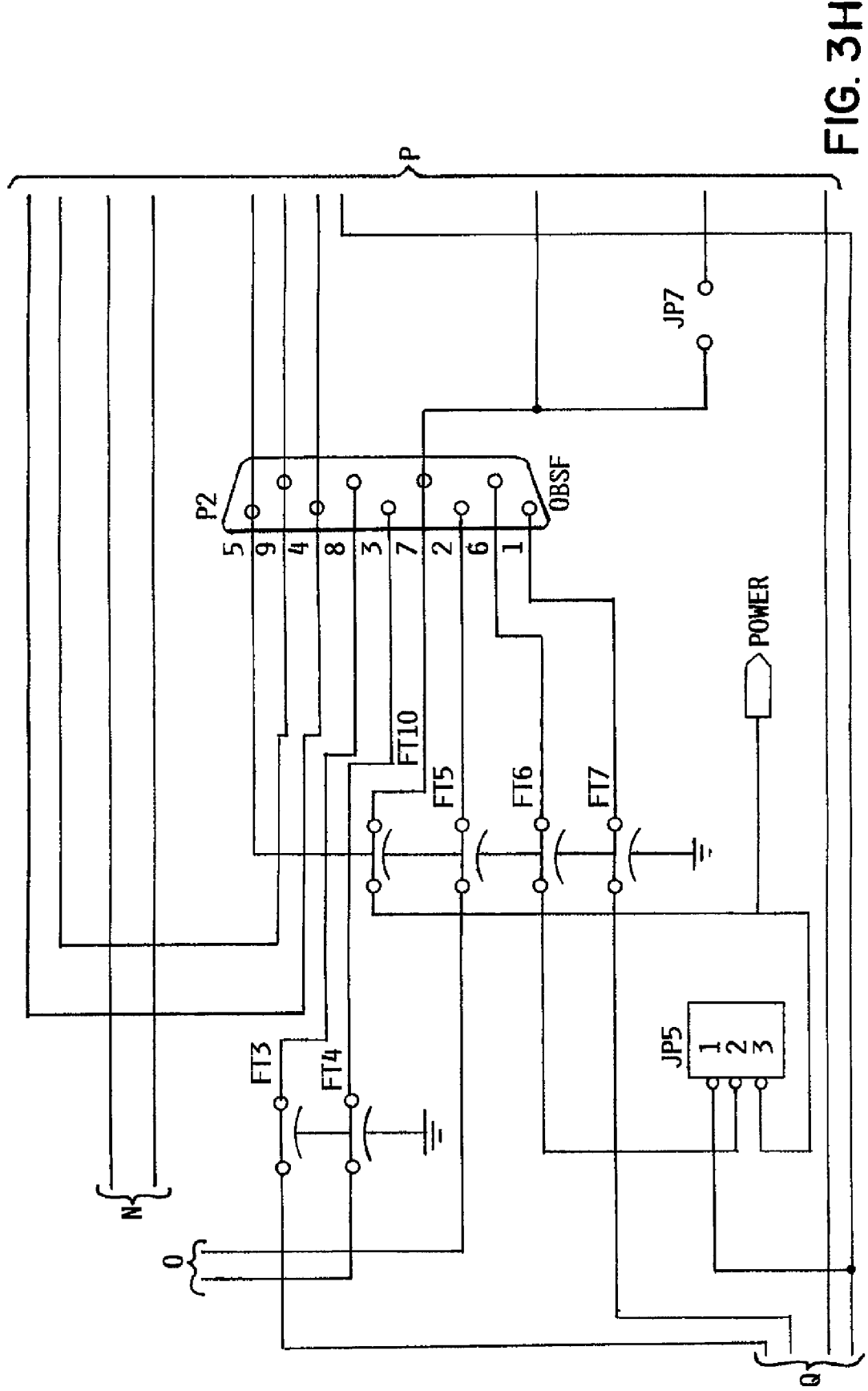
Figure 3I:
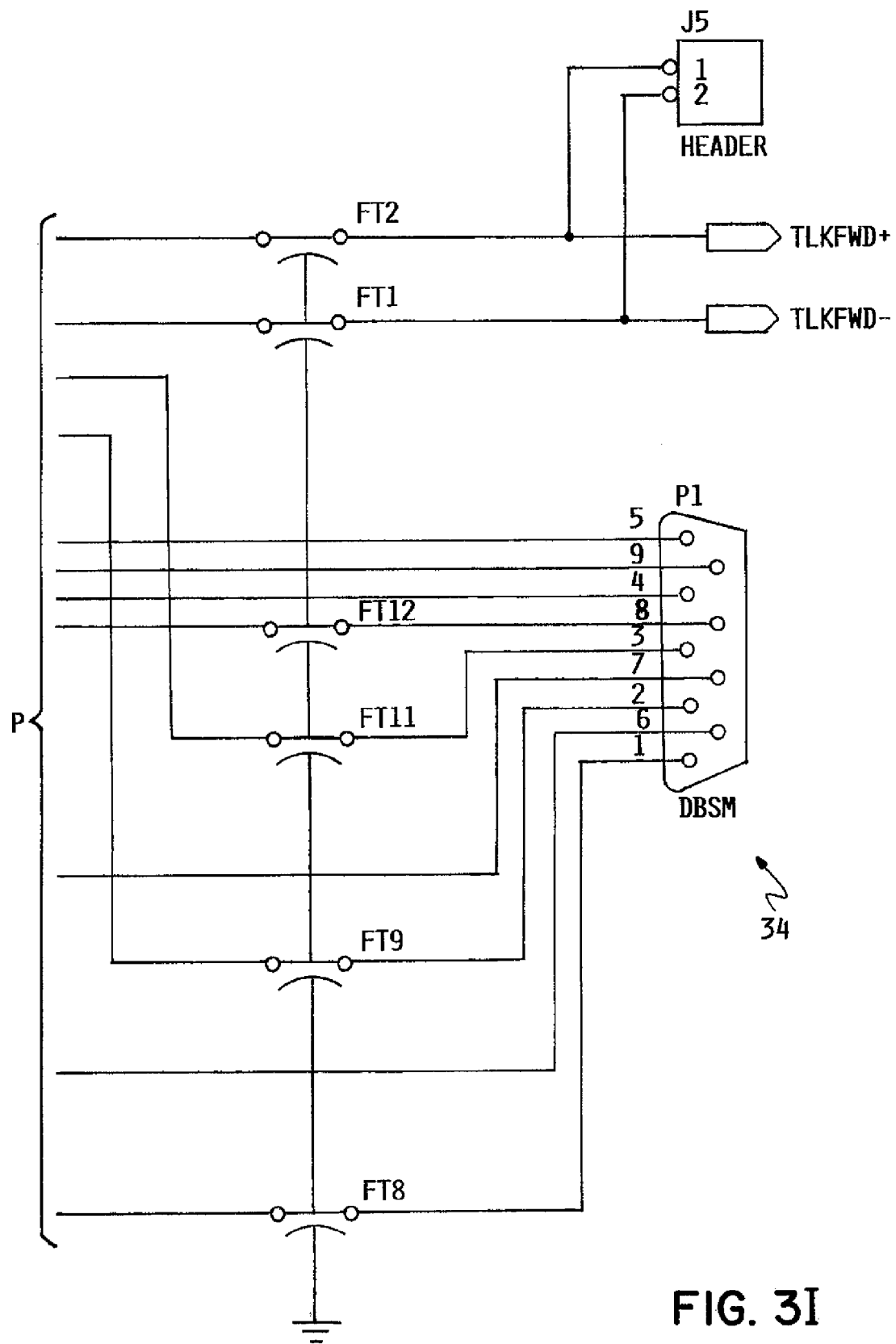
Figure 3J:
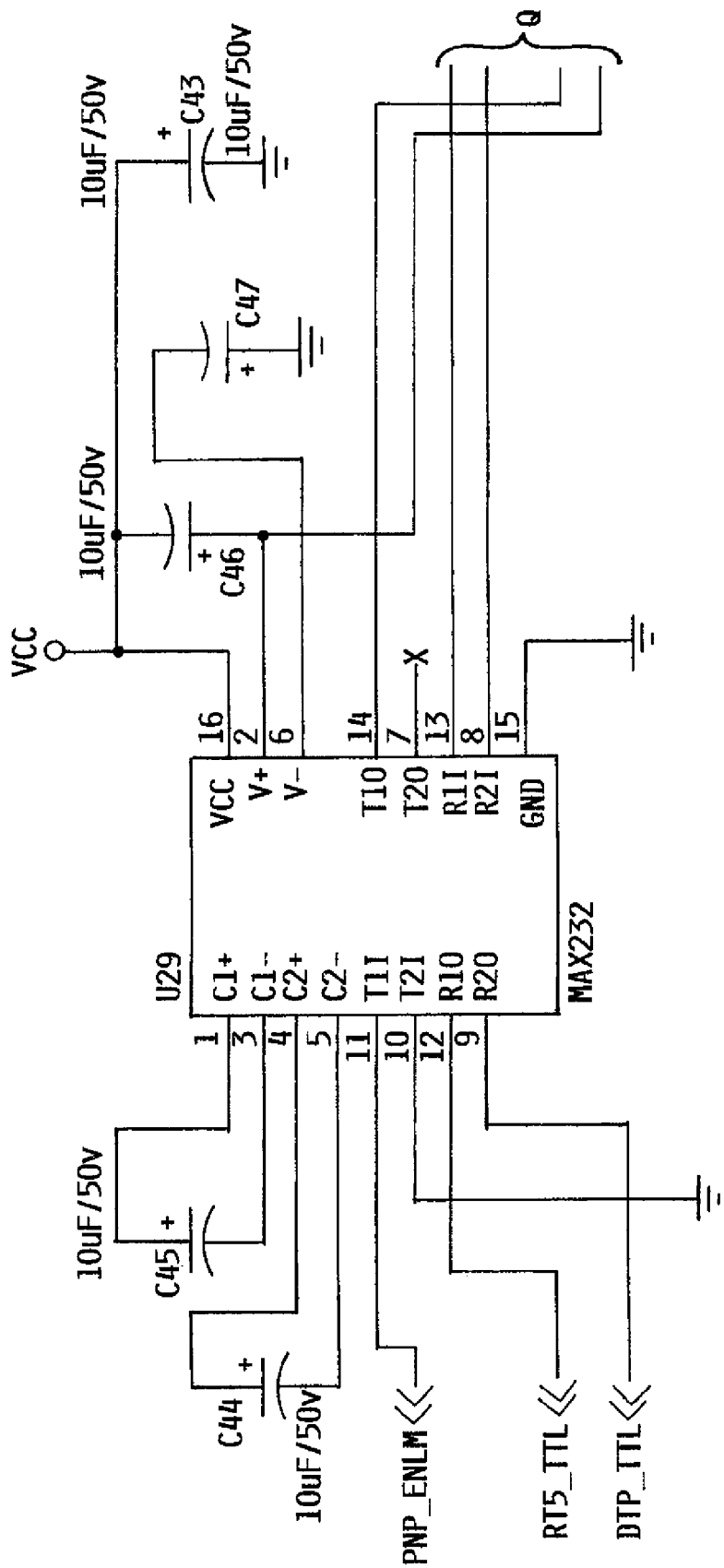
Figure 4A:
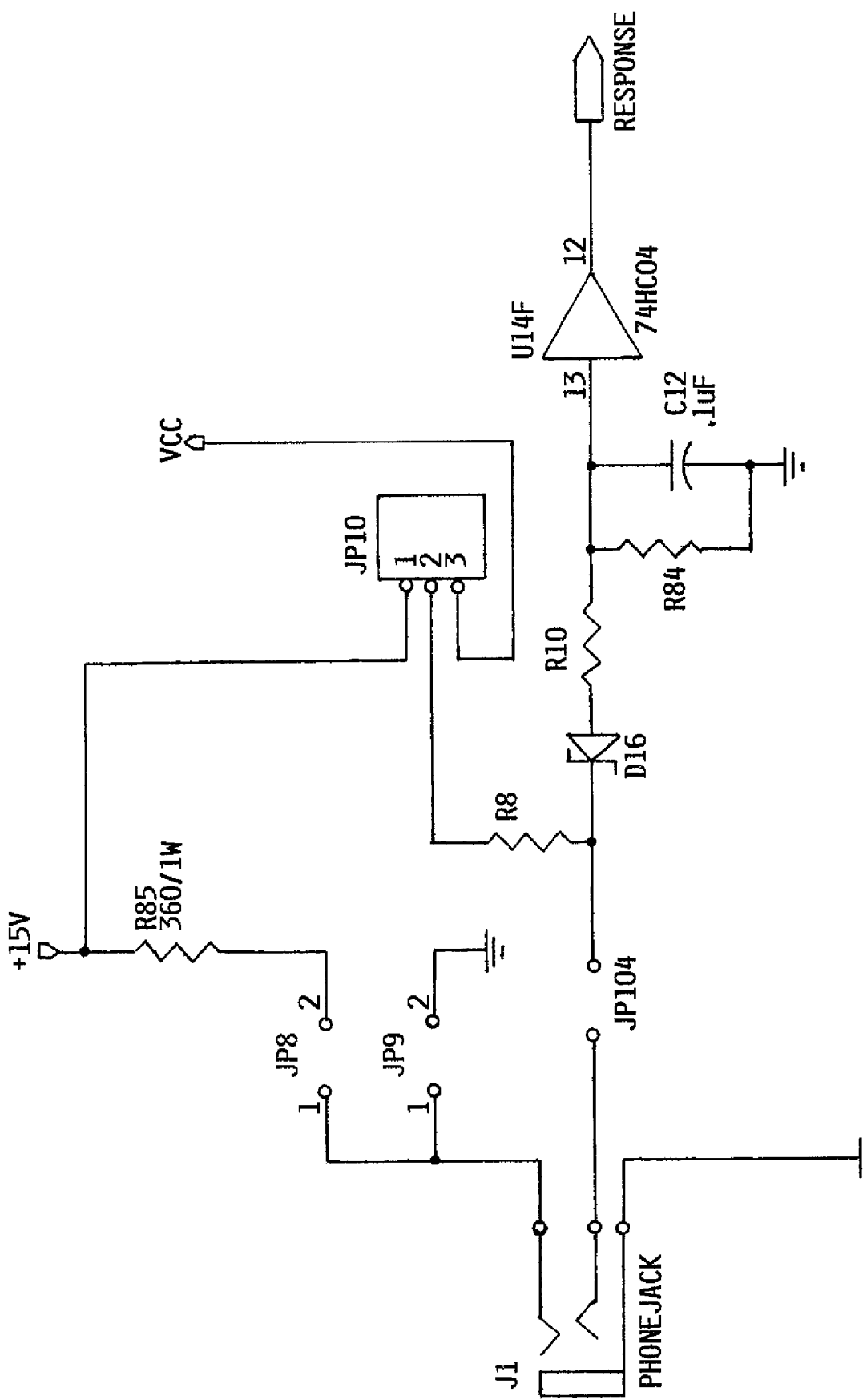
FIGS. 4A-4G are each a portion of a schematic circuit diagram of a CPU input/output section of the audiometer of FIG. 2.
Figure 4B:
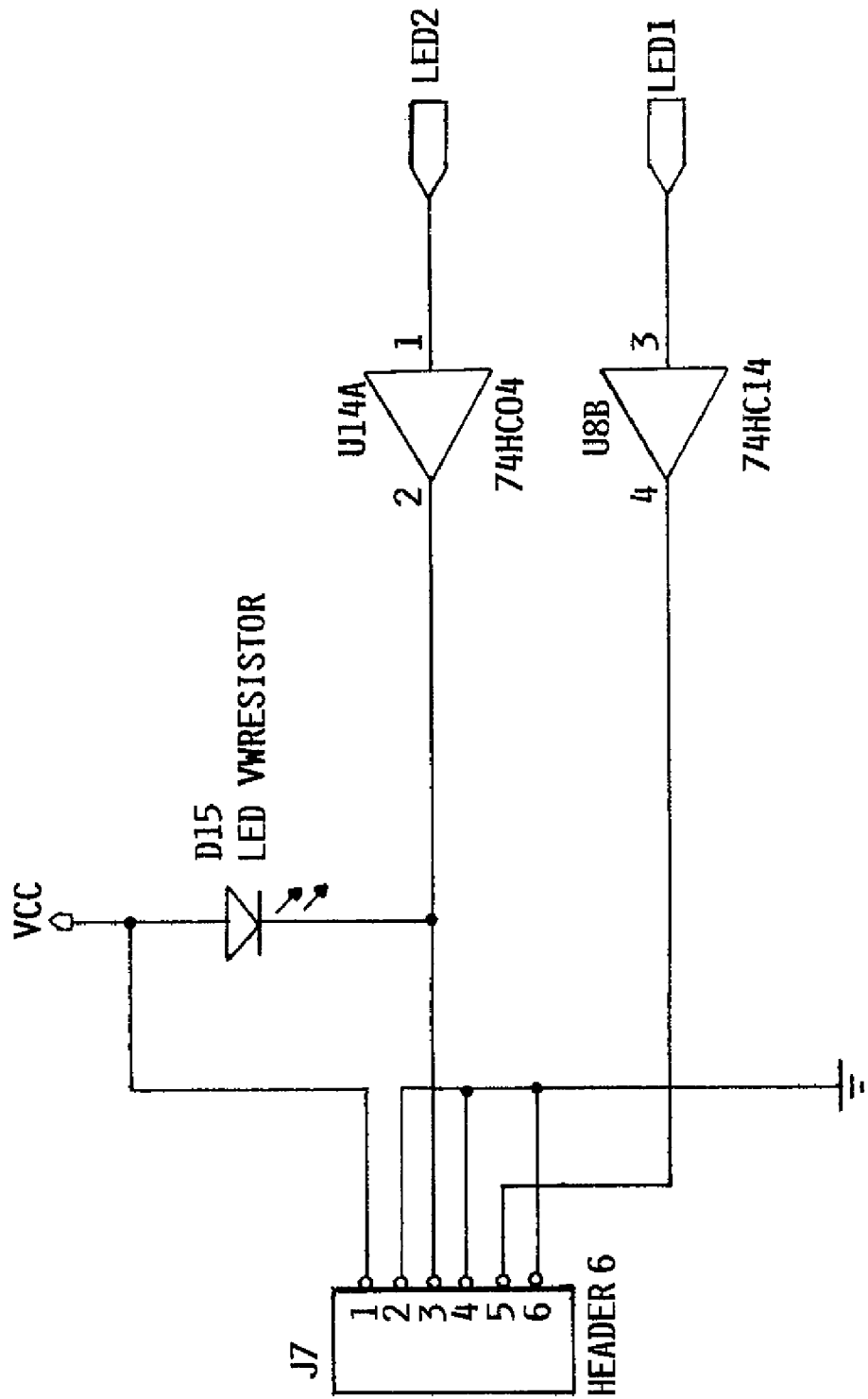
Figure 4C:
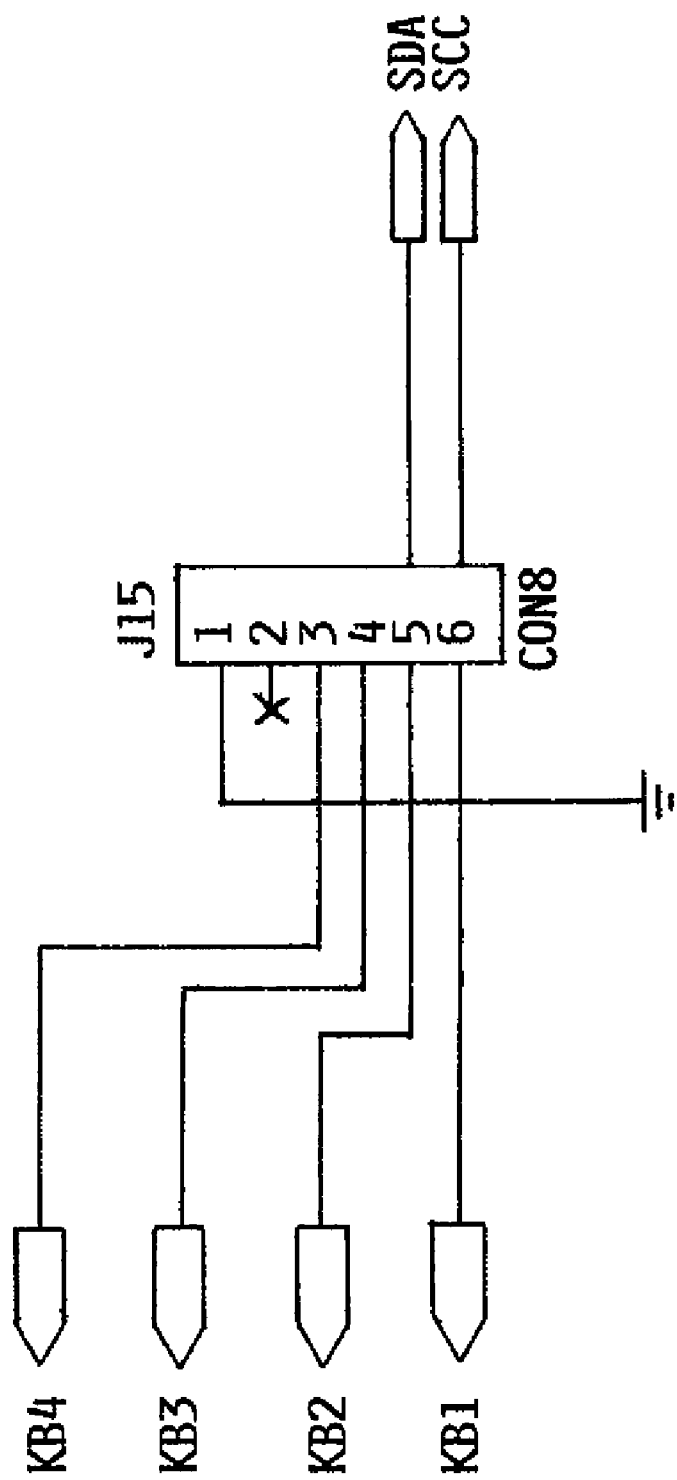
Figure 4D:
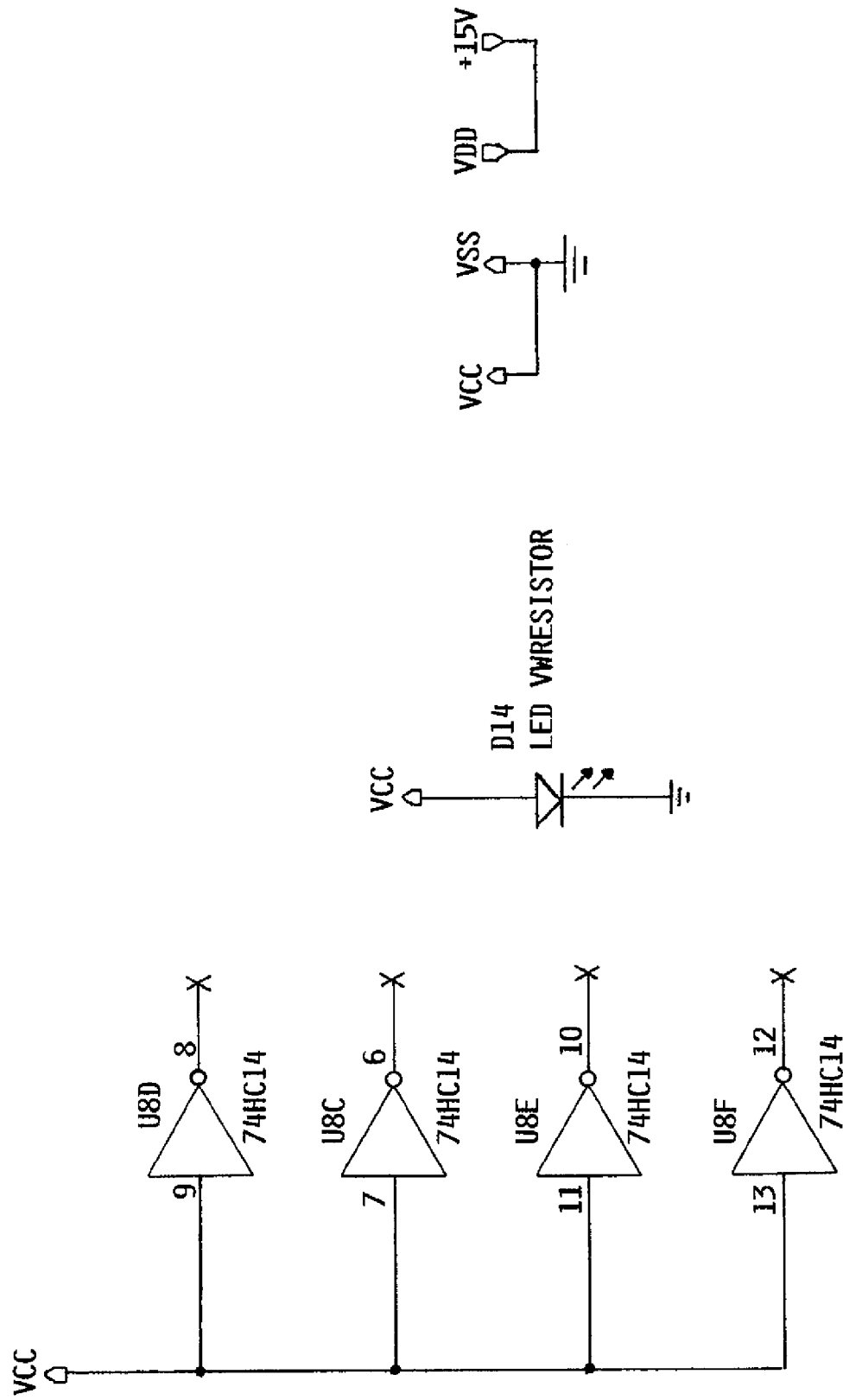
Figure 4E:
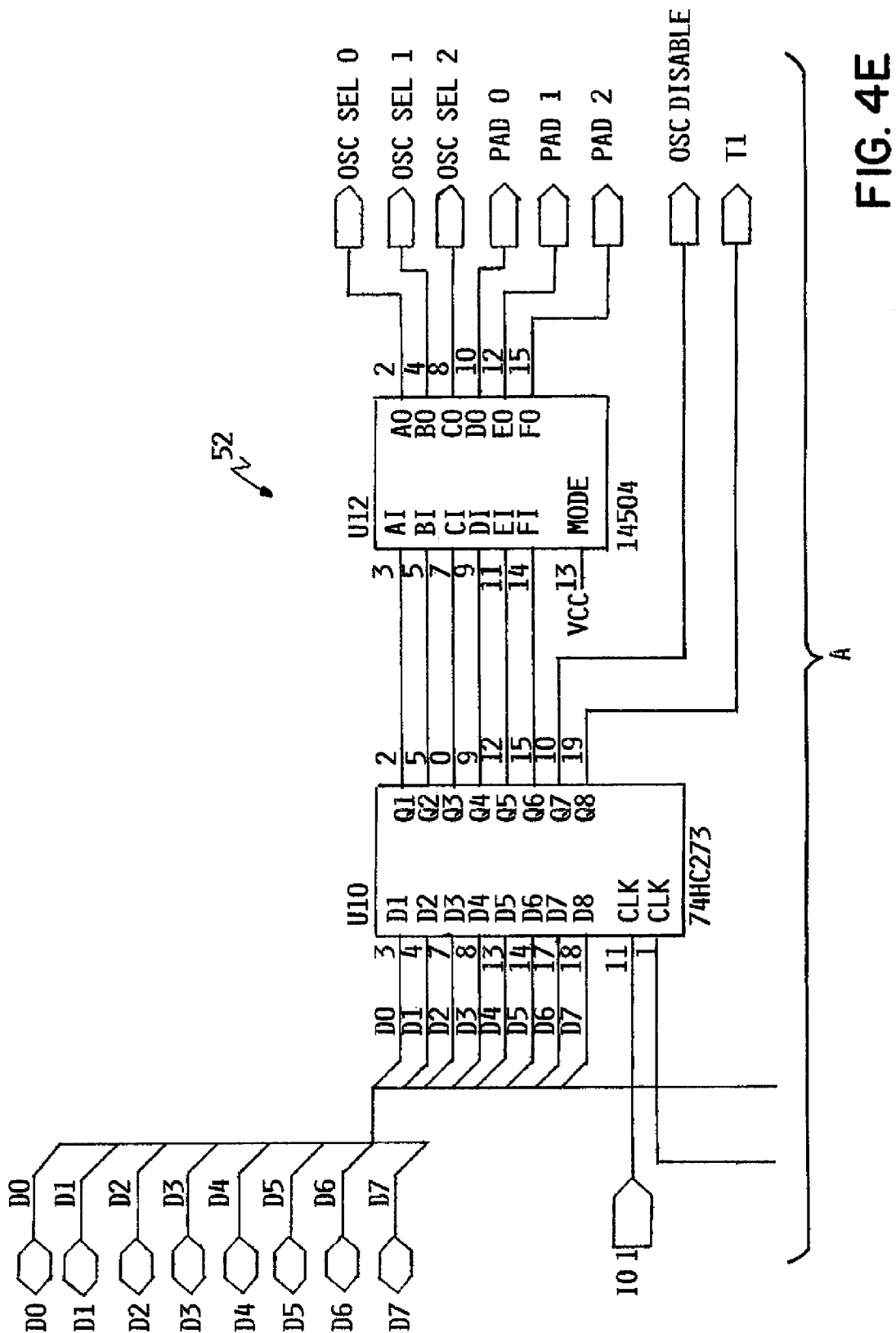
Figure 4F:
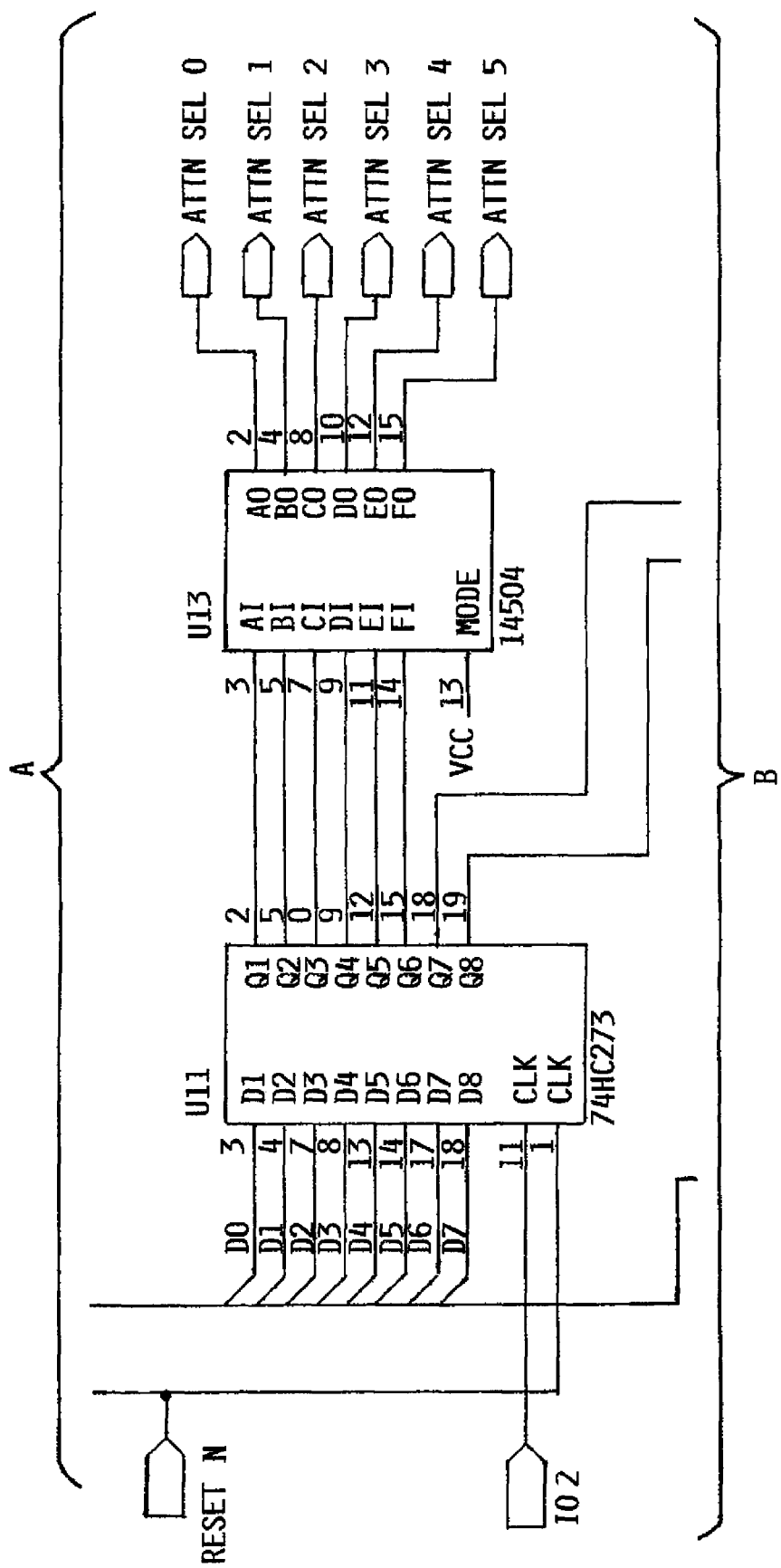
Figure 4G:
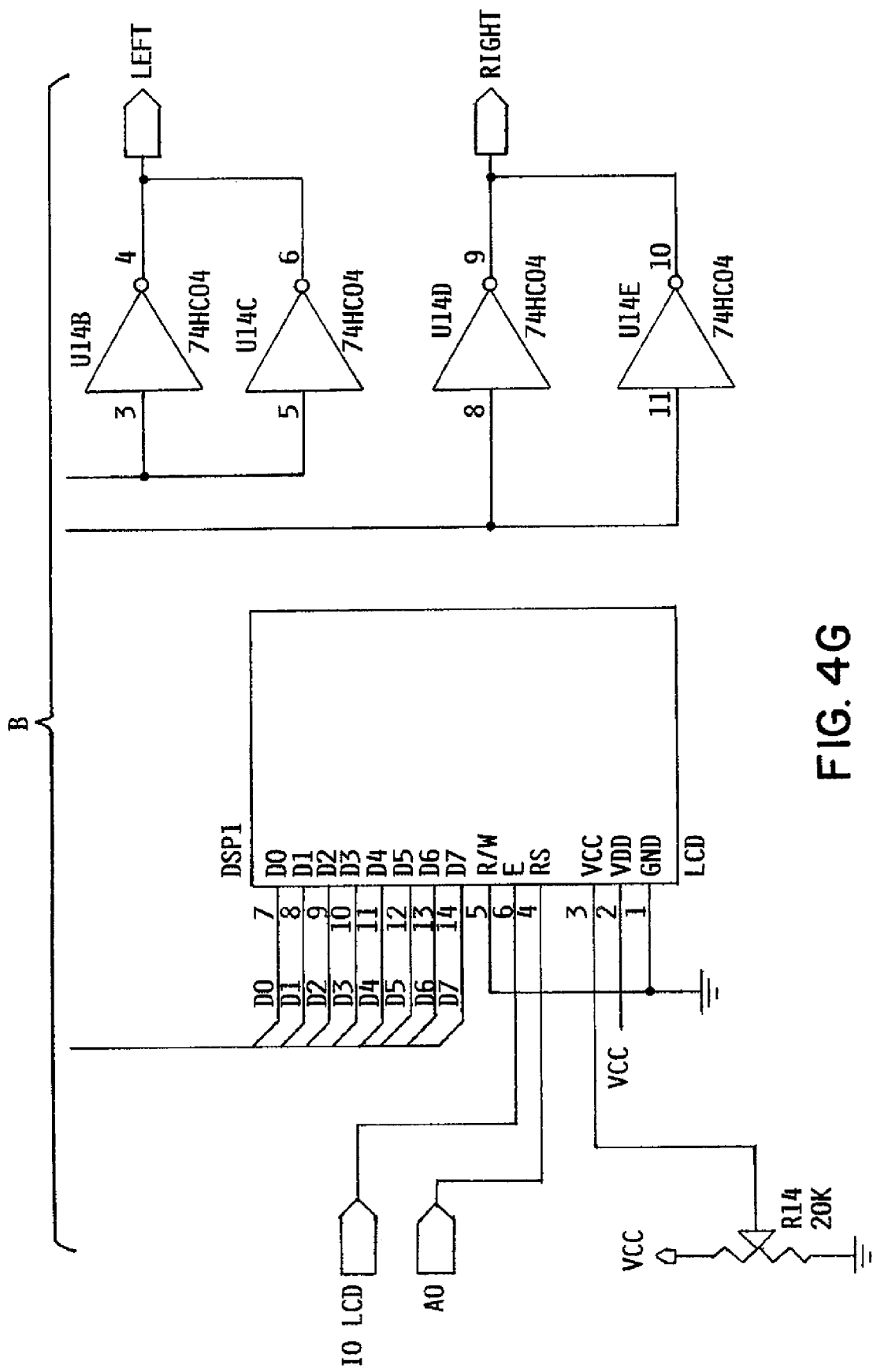
Figure 5A:
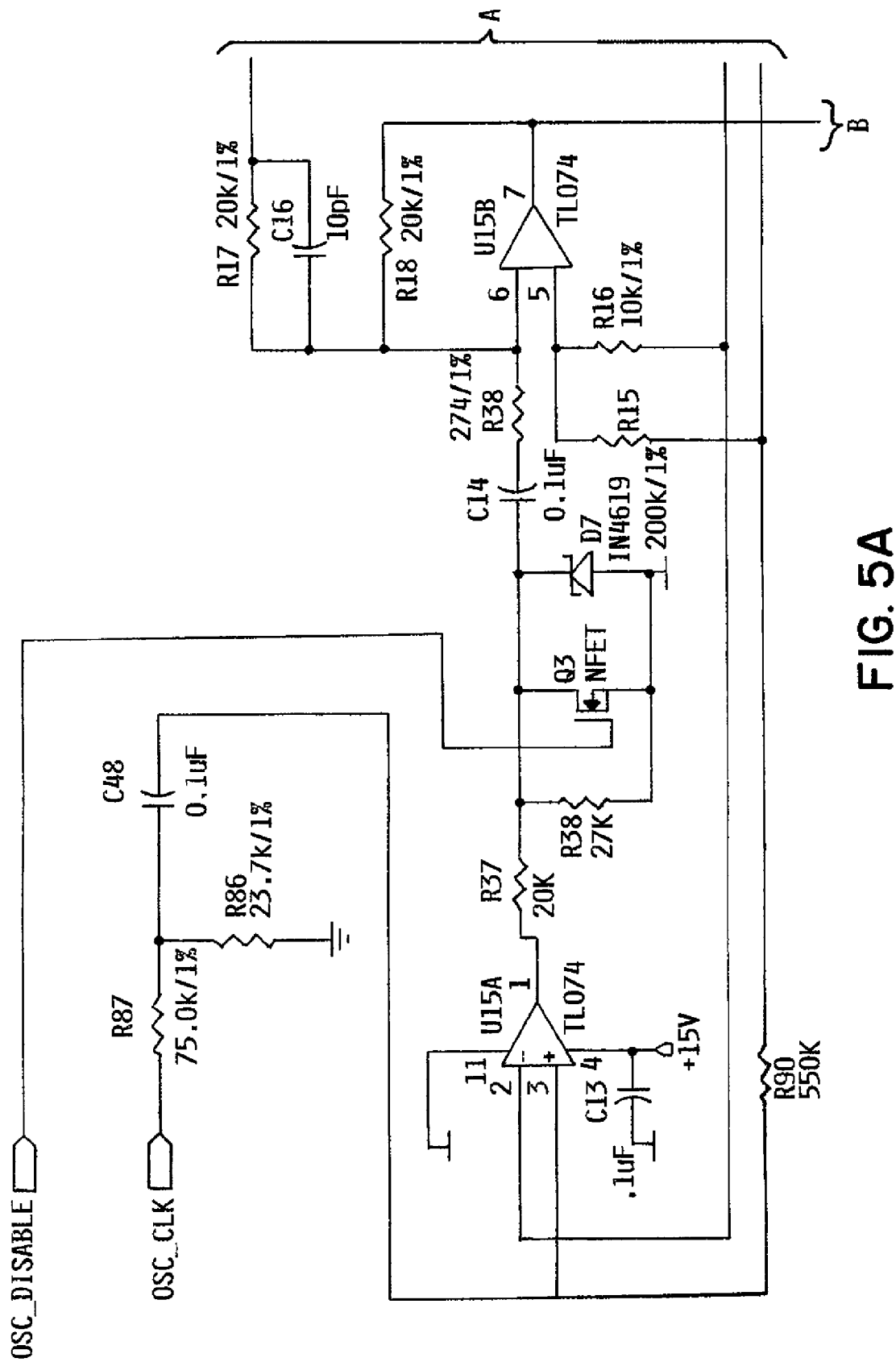
FIGS. 5A-5D are each a portion of a schematic circuit diagram of an oscillator module of the audiometer of FIG. 2.
Figure 5B:
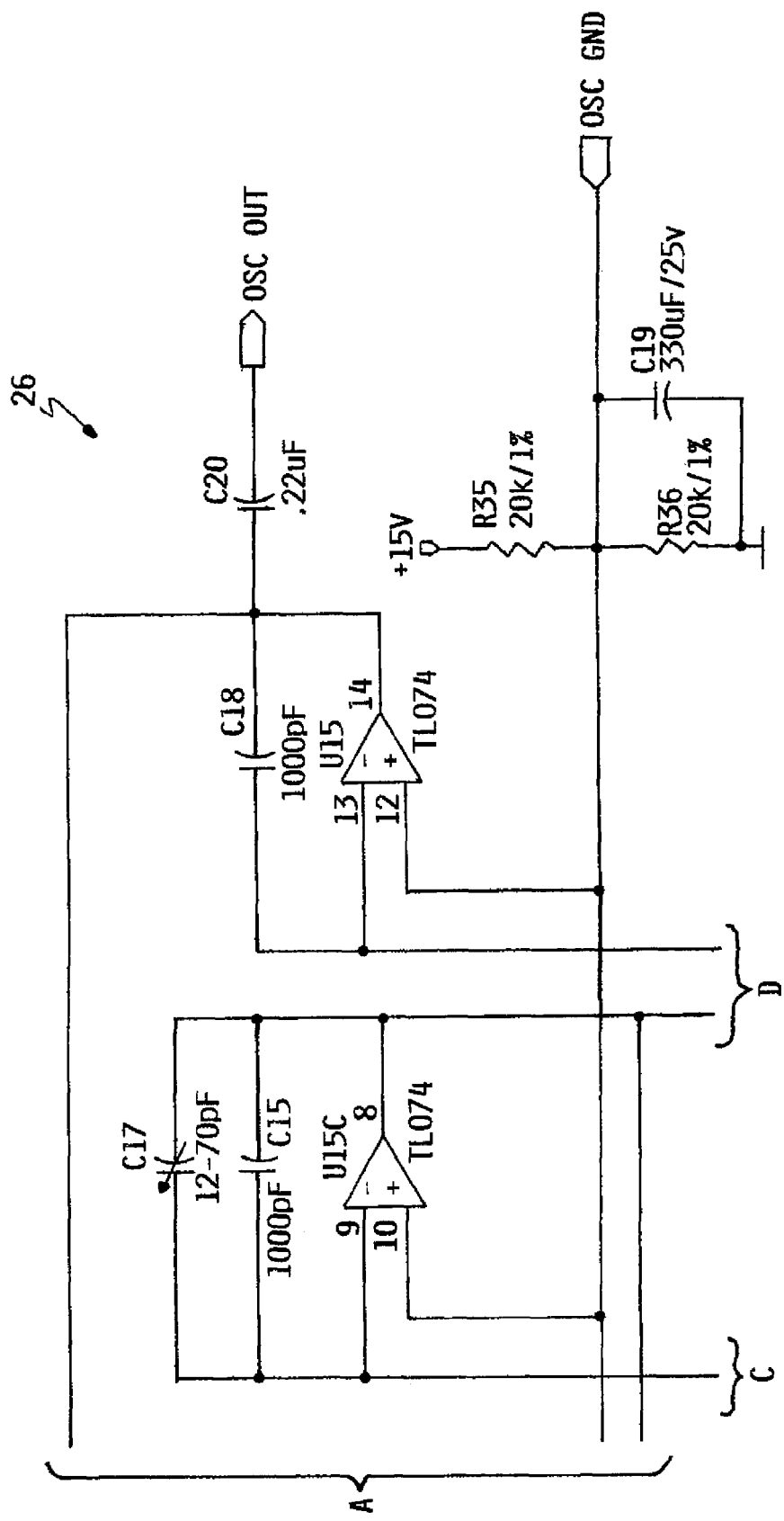
Figure 5C:
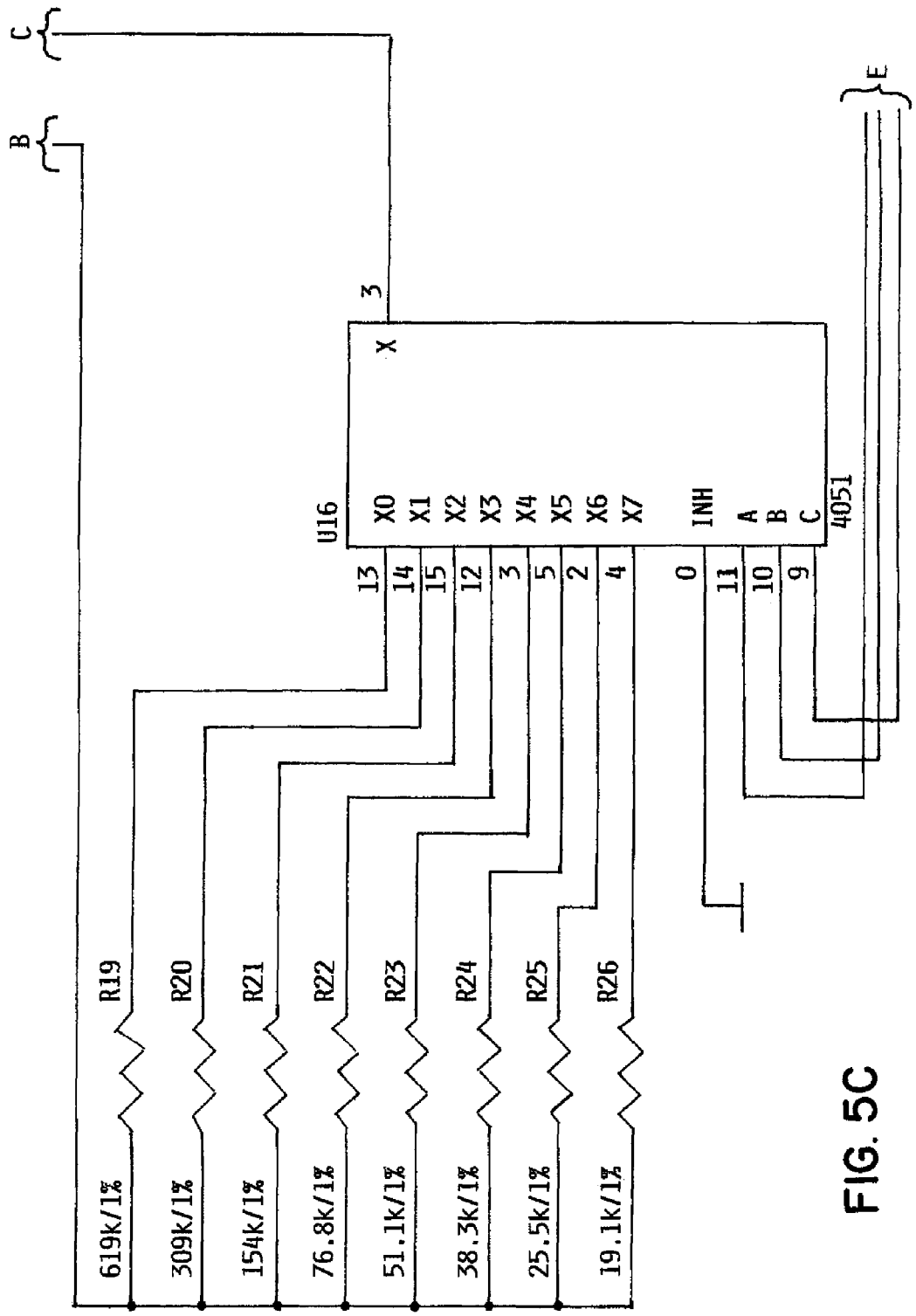
Figure 5D:
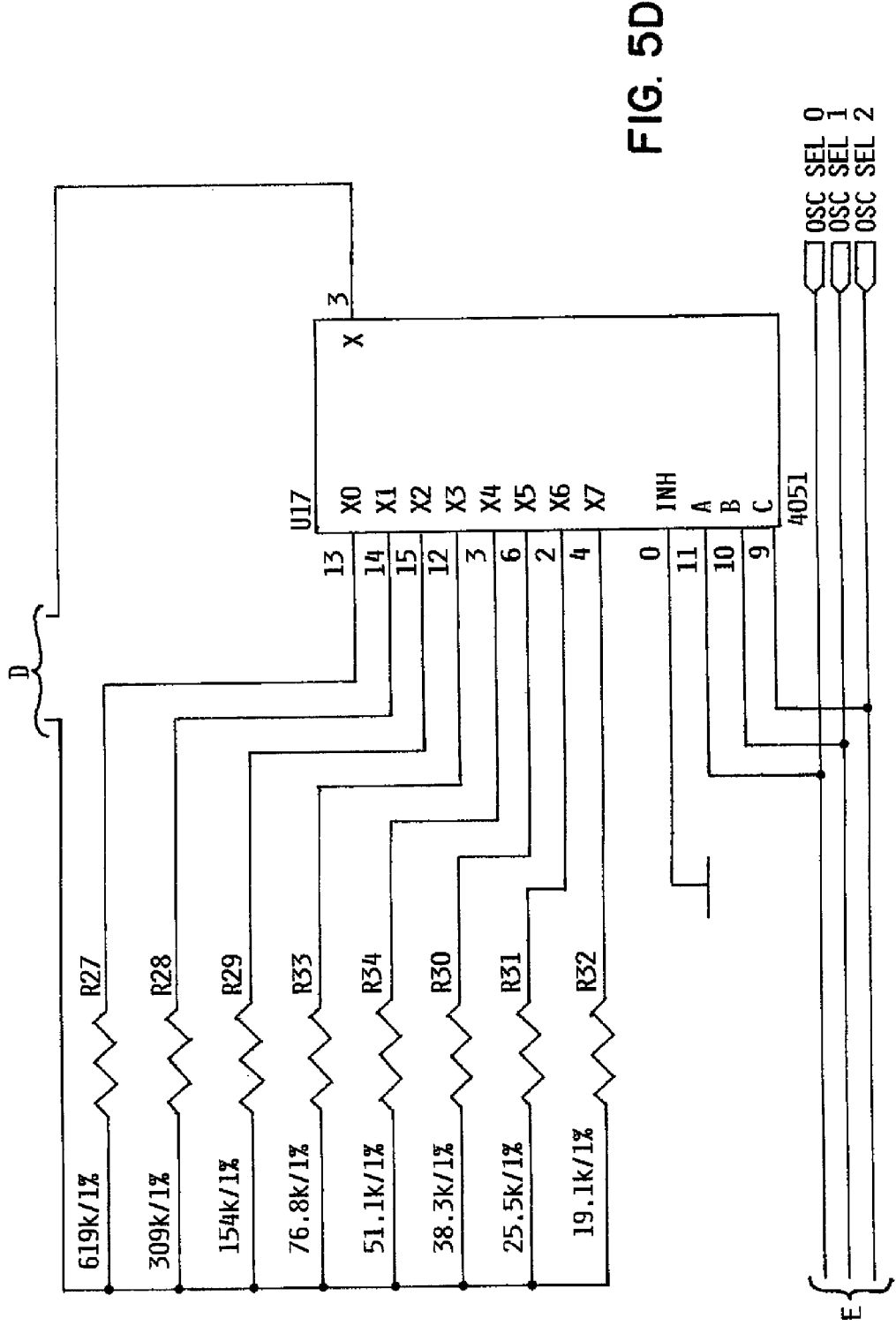
Figure 6A:
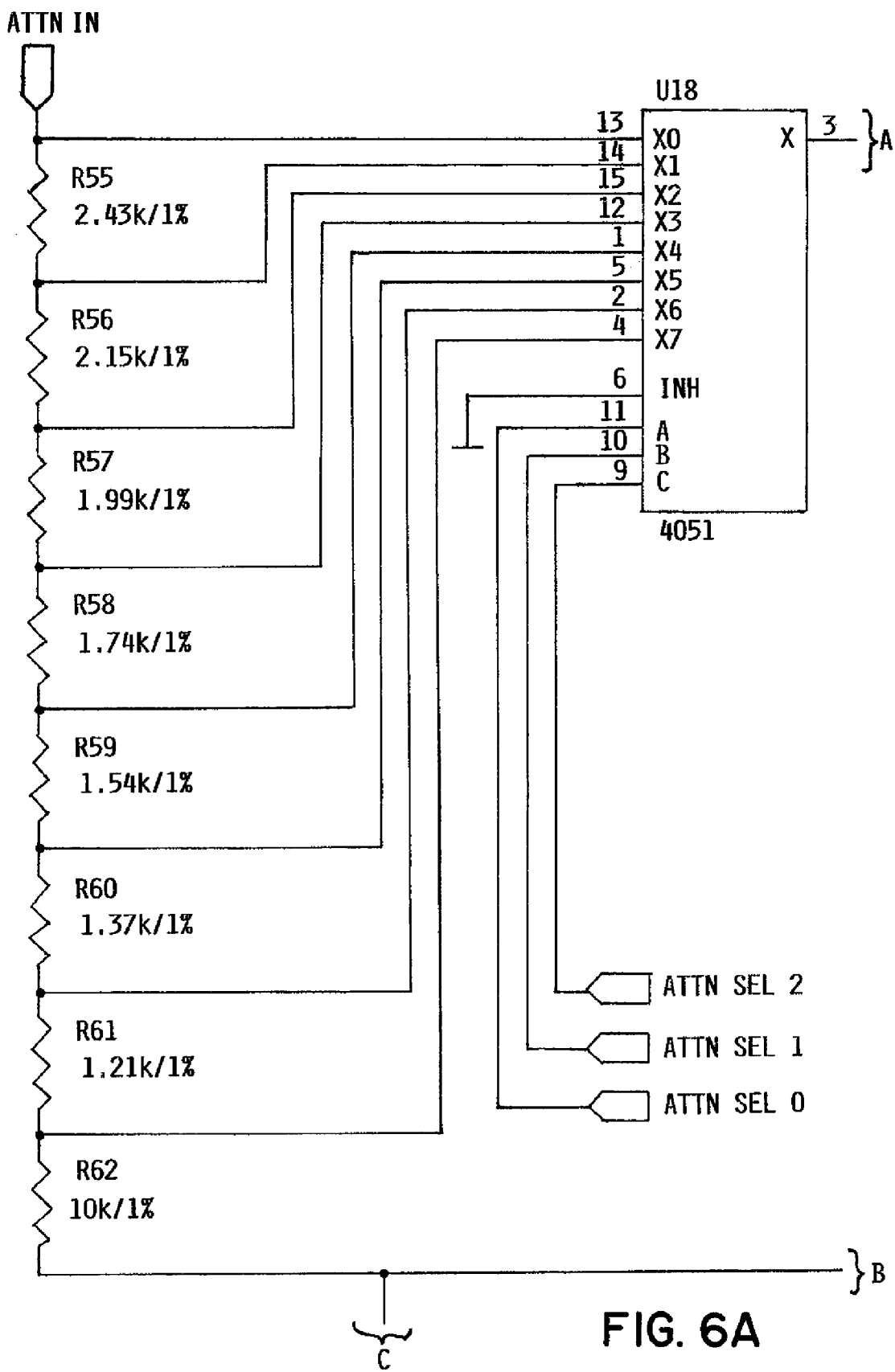
FIGS. 6A-6D are each a portion of a schematic circuit diagram of an attenuator module of the audiometer of FIG. 2.
Figure 6B:
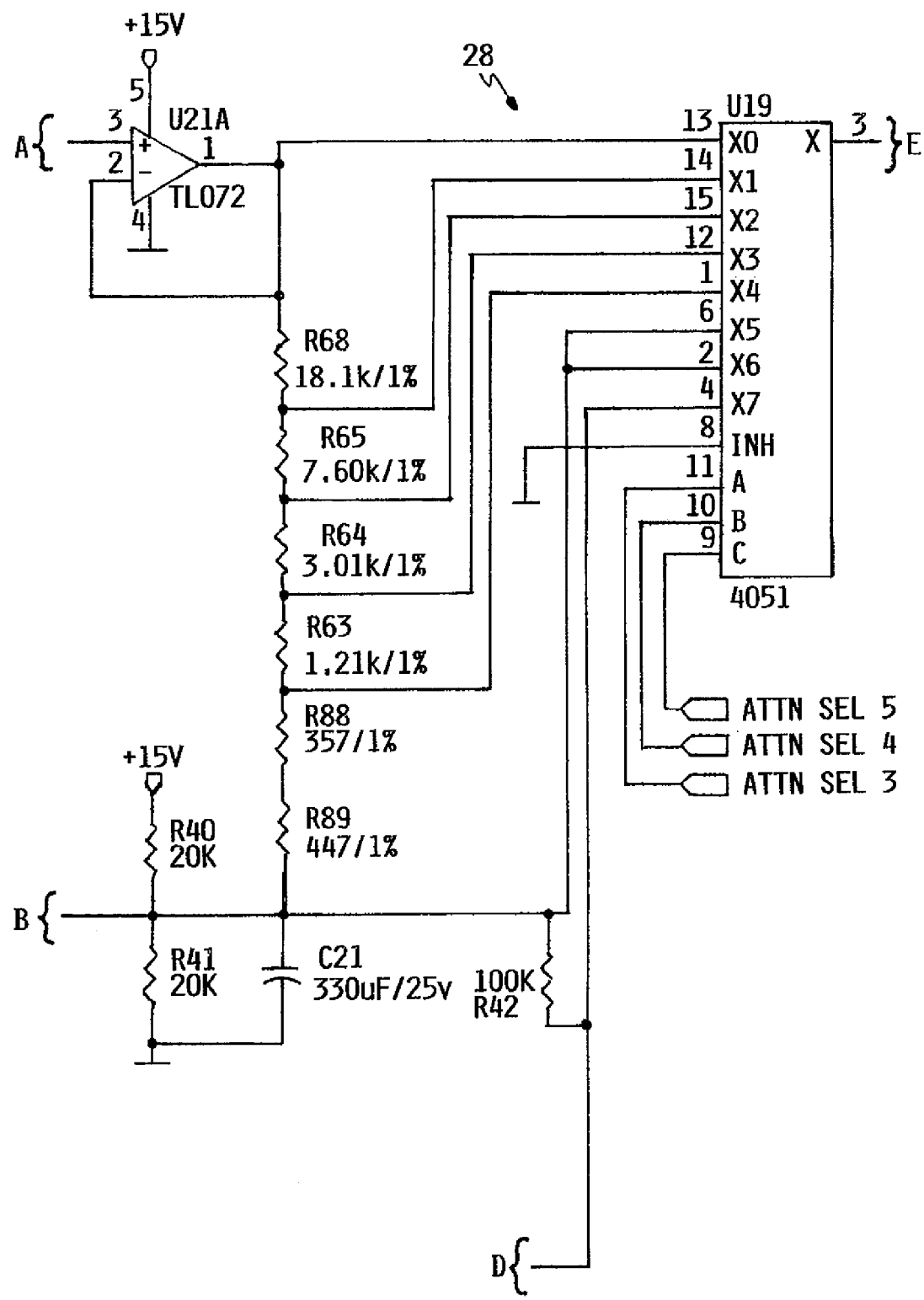
Figure 6C:
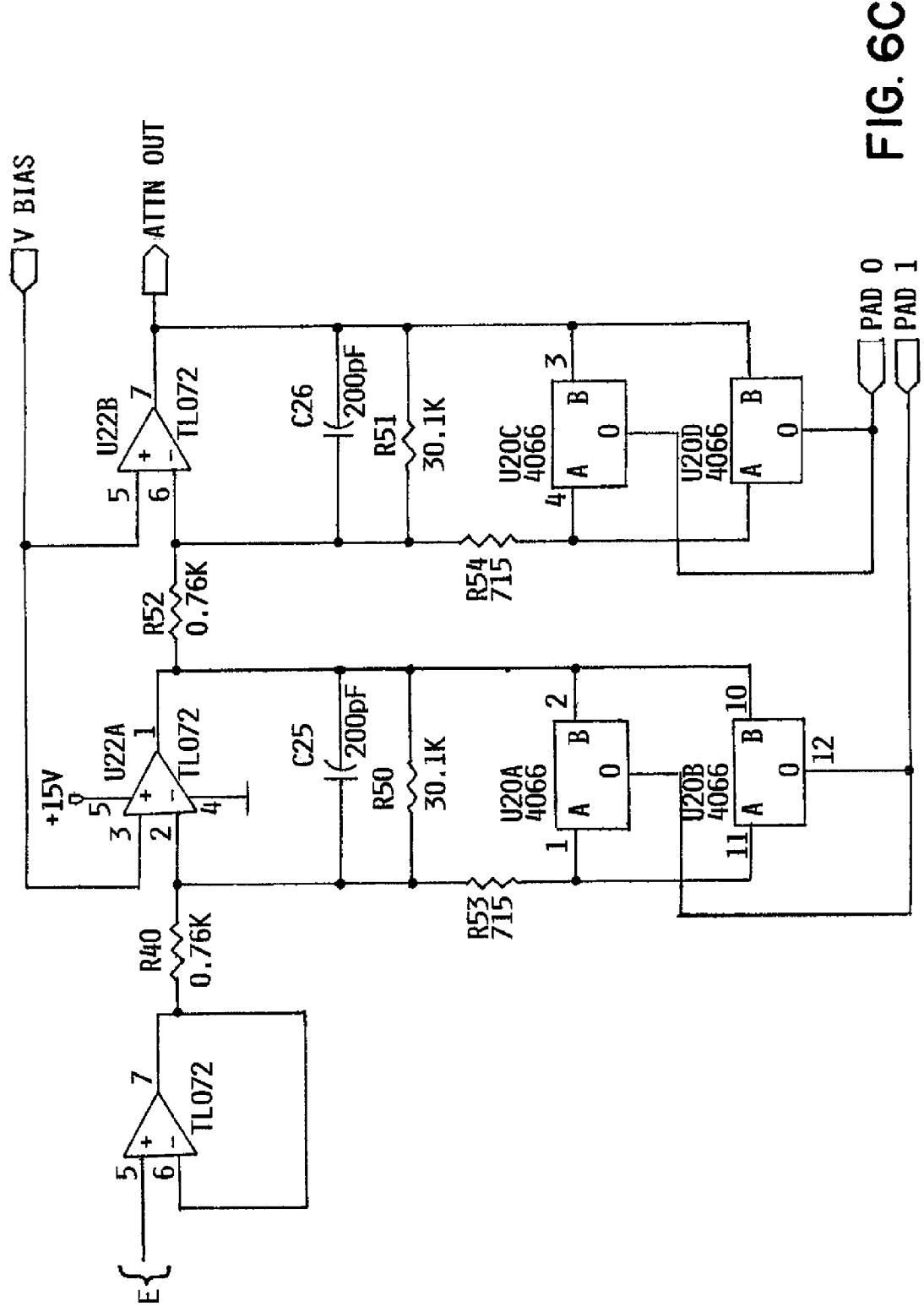
Figure 6D:
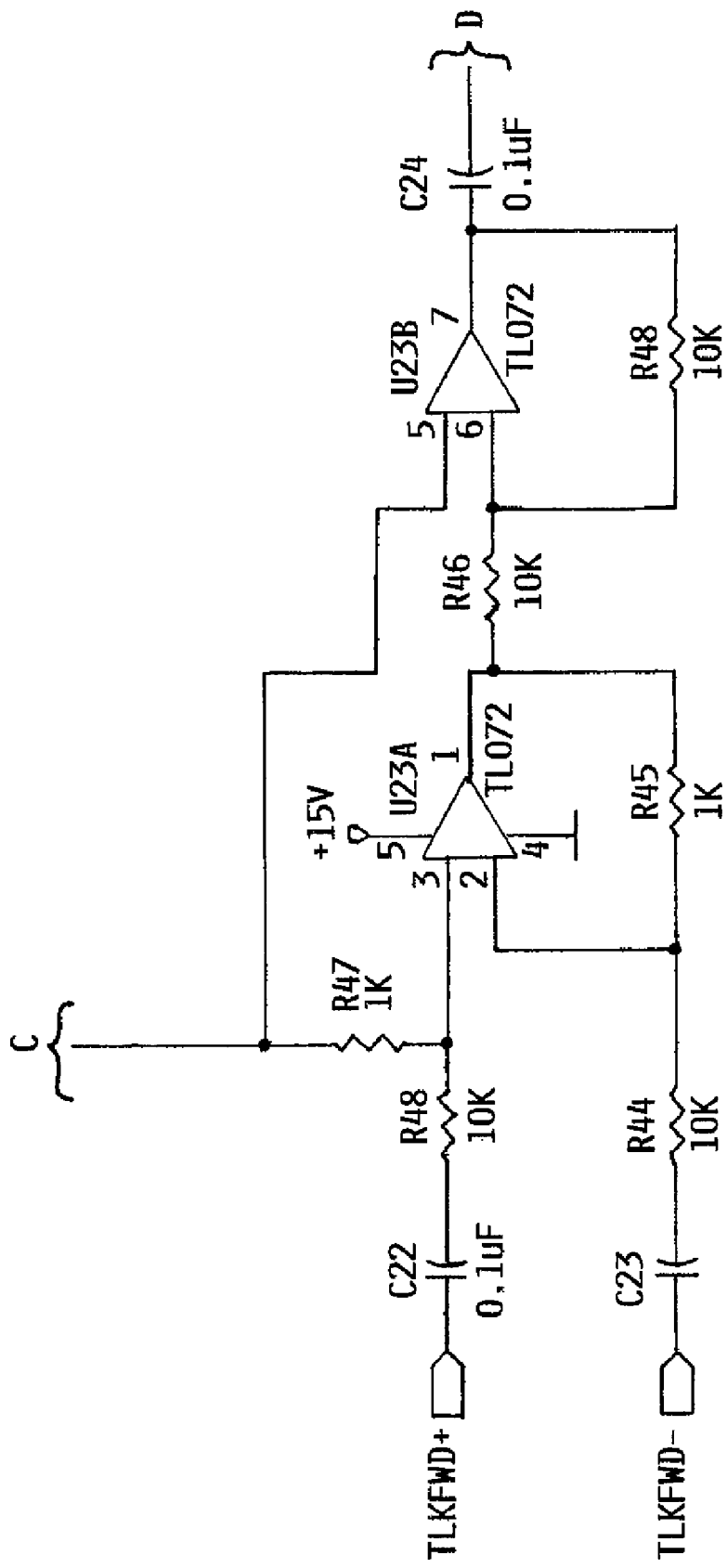
Figure 7A:
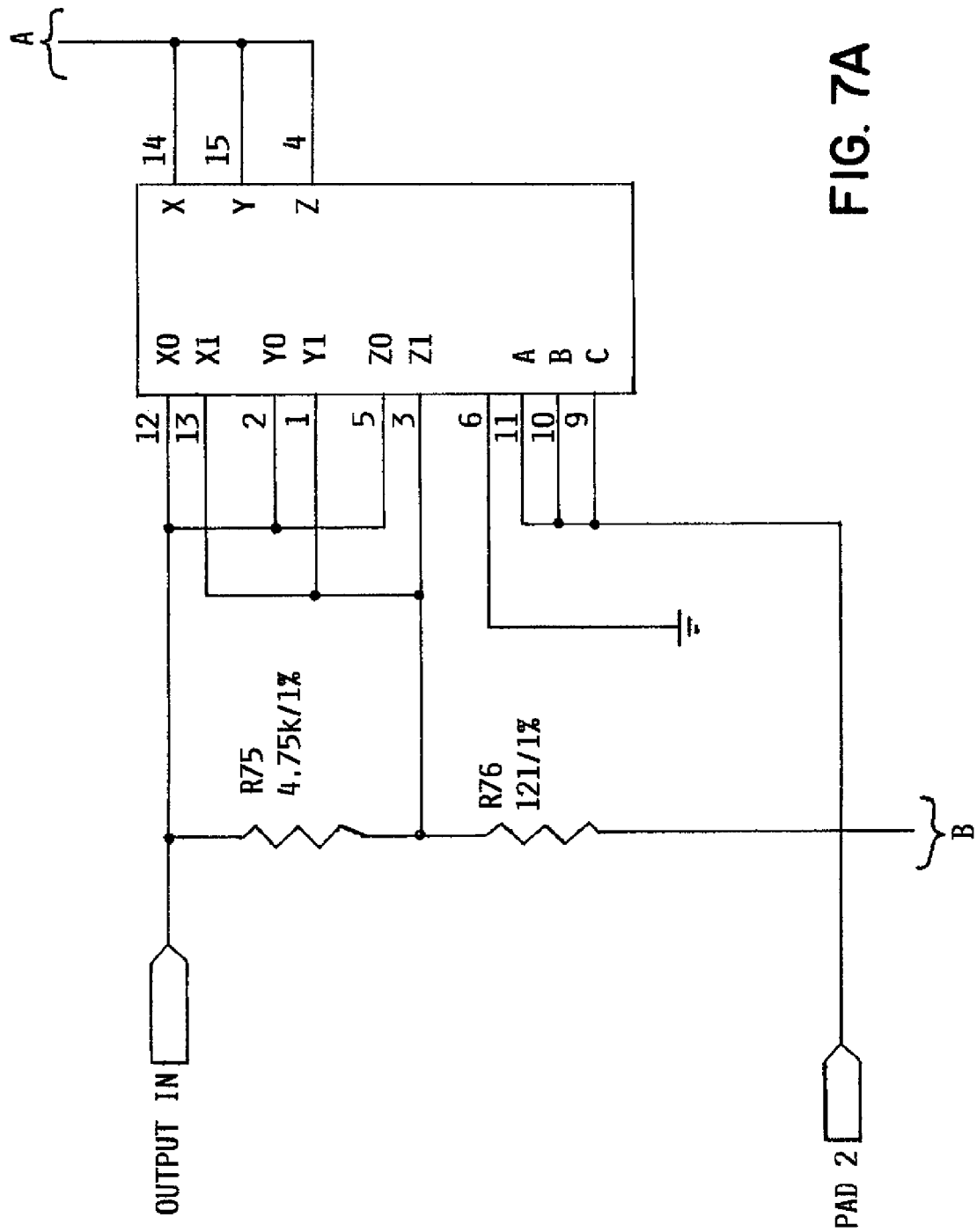
FIGS. 7A-7E are each a portion of a schematic circuit diagram of an output module of the audiometer of FIG. 2.
Figure 7B:
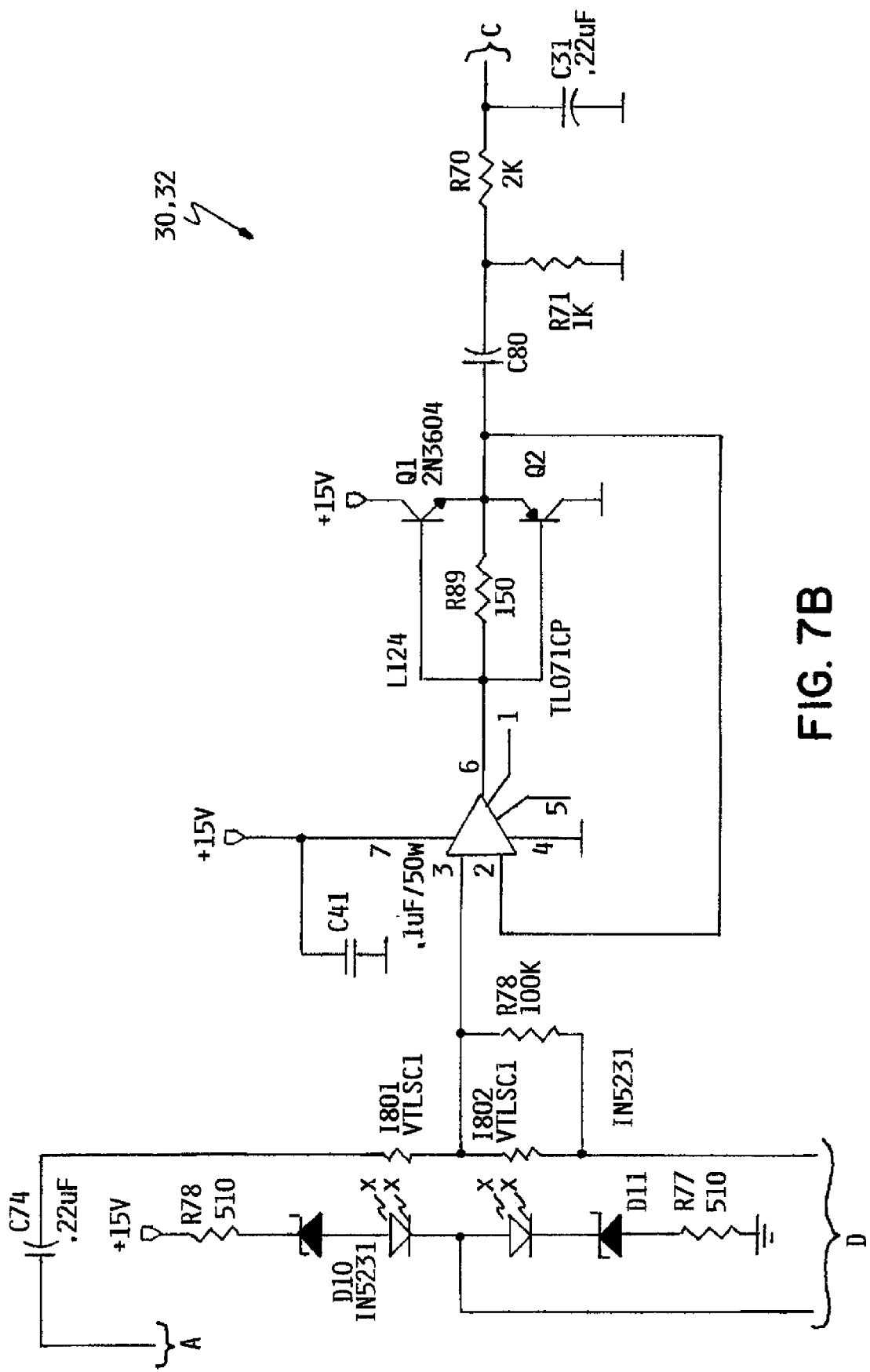
Figure 7C:
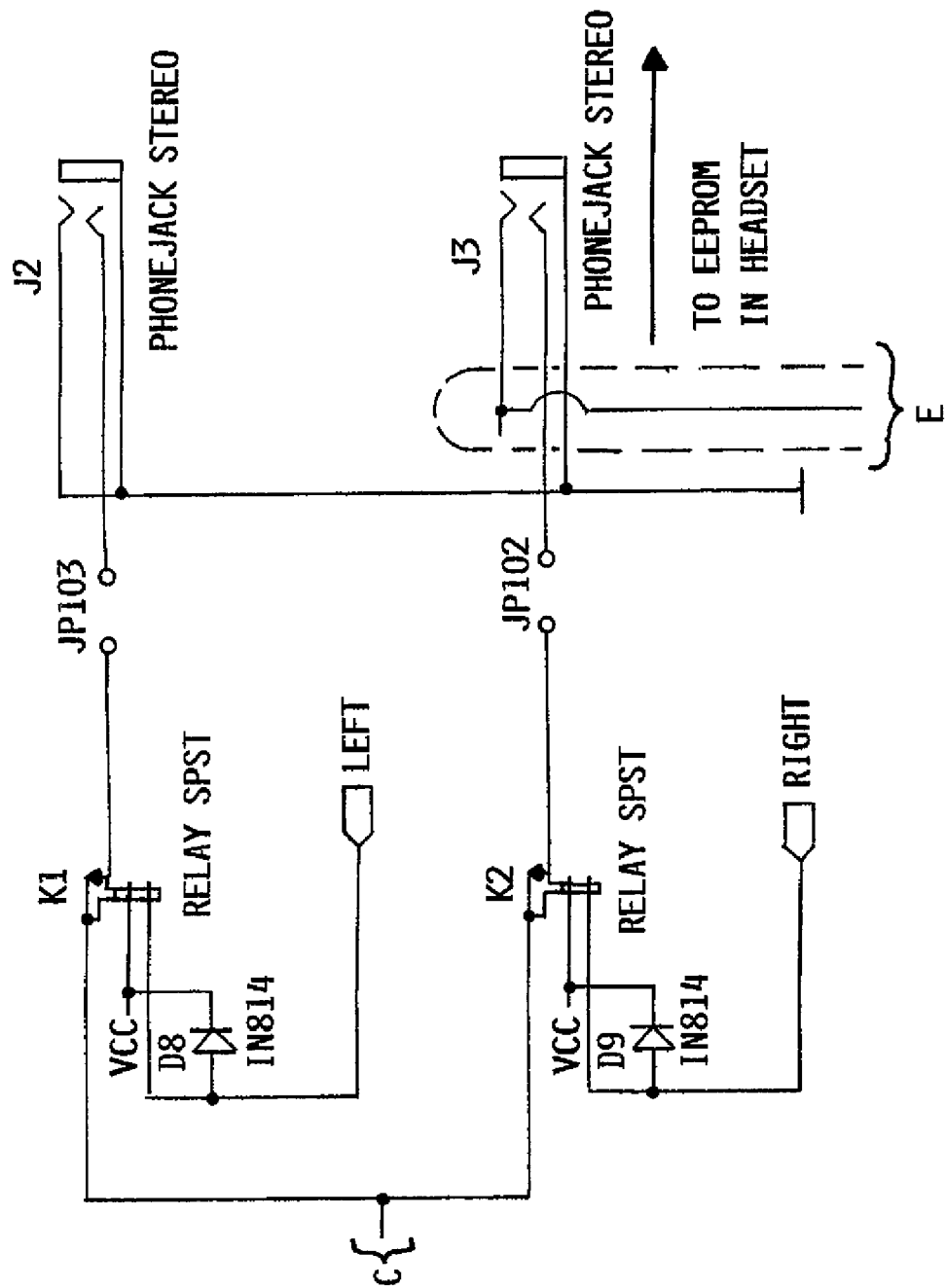
Figure 7D:
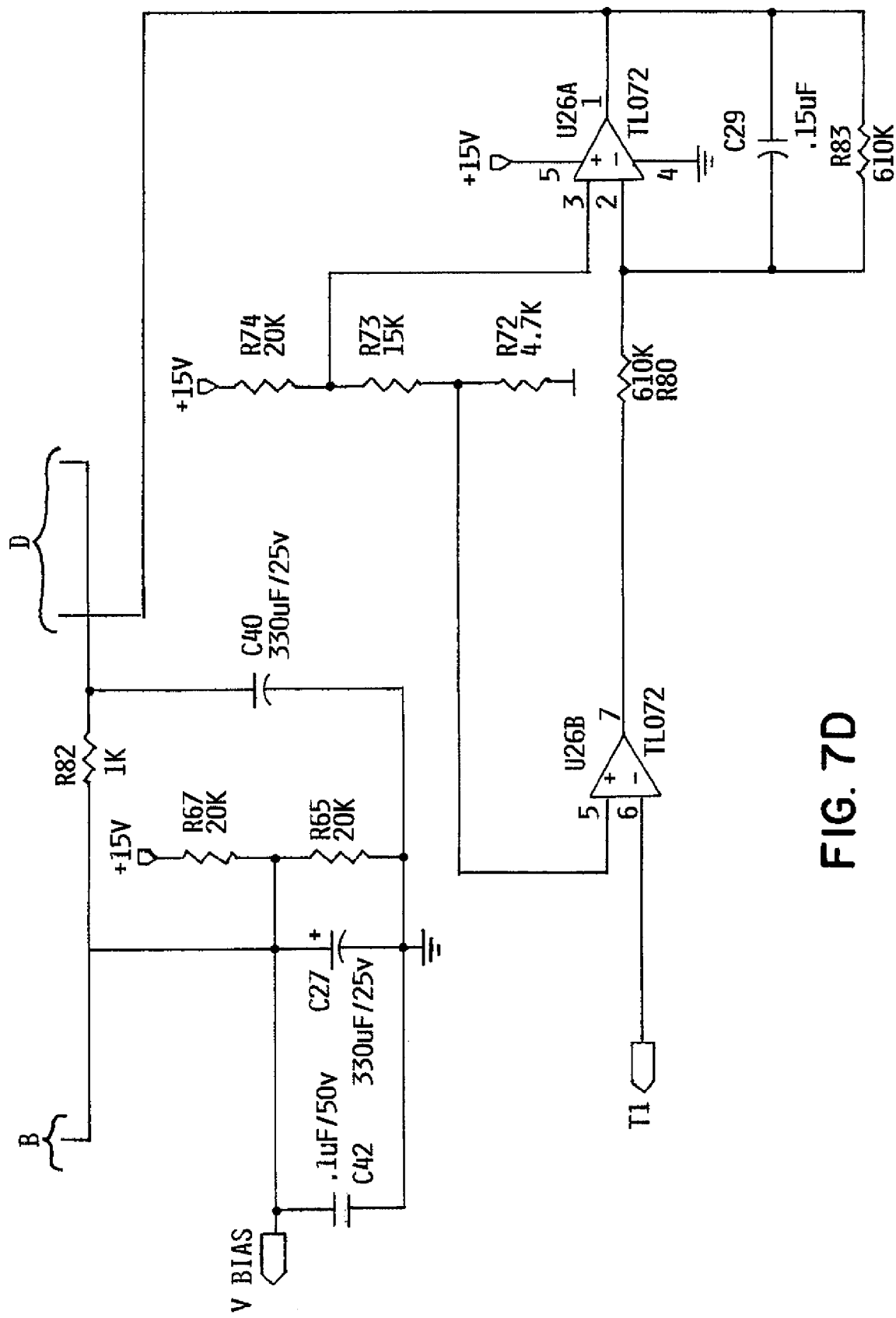
Figure 7E:
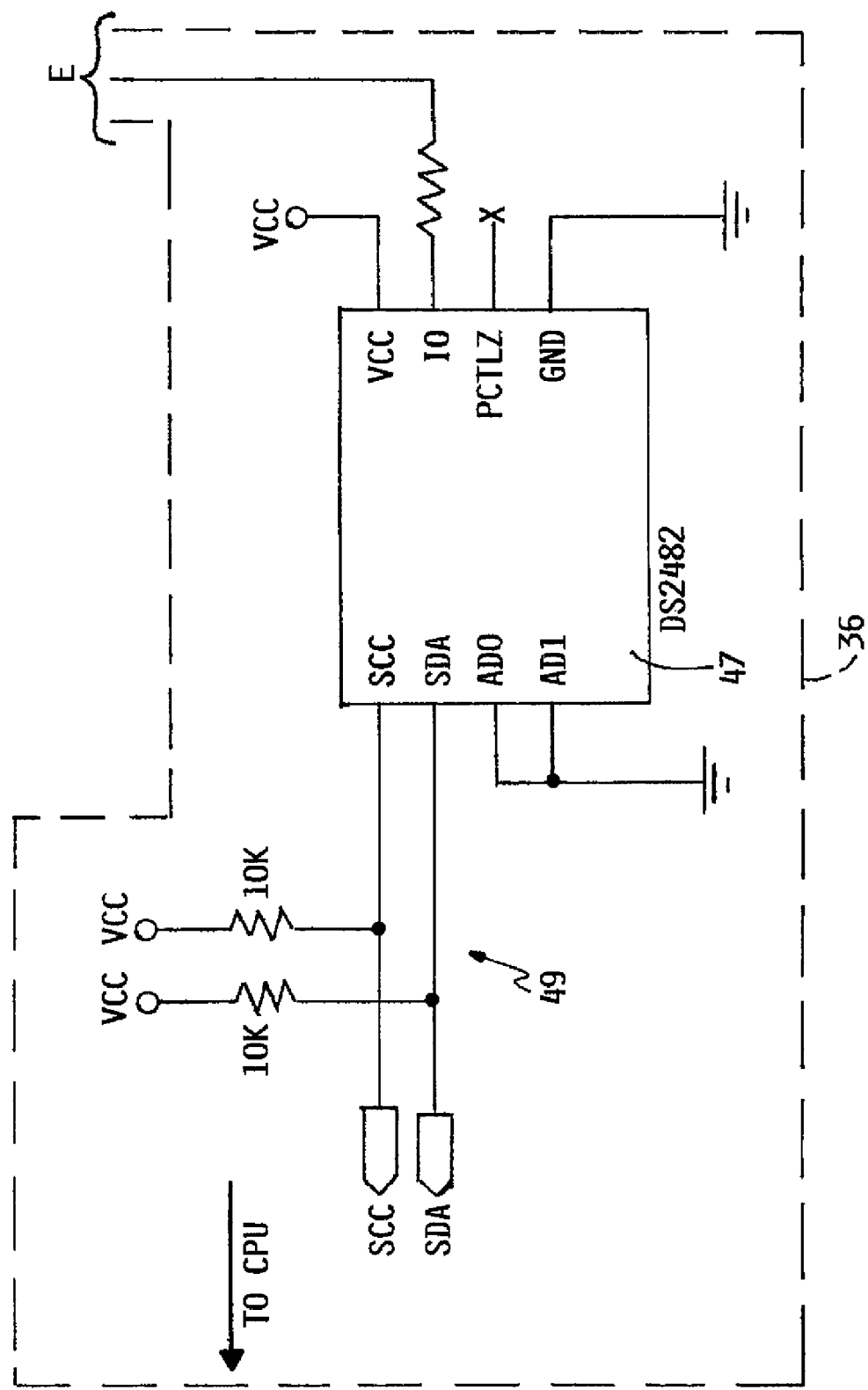

Transducer set 23 is connected to audiometer module 22 with left input jack 38 received in left signal output 30 and right input jack 40 in right signal output 32. As depicted in FIG. 1A, and as generally known in the art, audiometer module 22 can be controlled by a personal computer 54, which may include one or more input devices in the form of a keyboard and/or mouse 56 and a device for presenting information to an operator such as video display 58.

Typically, audiometer module 22 and transducers 24 are operated to provide automatic pure-tone hearing threshold testing in accordance with accepted audiometric procedures, such as for example, the well-known Hughson-Westlake procedure. In one example, CPU module 34 may be programmed to position channel selector switch 29A to left signal output 30 and to cause oscillator 26 to generate a first test tone of 1 kHz. CPU module 34 then controls magnitude selector switches 28B of attenuator 28 to present the 1 kHz tone to the left ear of the test subject through left input jack 38 of transducer 24 at a series of specified magnitudes (e.g. 70 dB, 60 dB, 50 dB, 40 dB, 30 db, and 20 dB). The test subject responds when the tone is perceived using handswitch 60, and the responses may be recorded by audiometer module 22 or personal computer 54. Once a threshold is established for the 1 kHz tone, the process is repeated for a series of different frequency tones (e.g. 500 Hz, 1 kHz, 2 kHz, 3 kHz, 4 kHz, 6 kHz, and 8 kHz.) to establish a threshold for each. CPU module 34 then shifts channel selector switch 29A to right signal output 32 and the entire process is repeated for the right ear of the test subject. It will of course be appreciated that CPU module 34 may be programmed to perform any other sequence or method of testing as may be desired.

In embodiments of the invention, all audiometer modules 22 of a given model may be initially standardized so as to produce a uniform, stable output signal, i.e., to generate an electrical output signal having a magnitude within a certain tolerance at any given tone frequency (e.g. 500 Hz, 1 kHz, 2 kHz, 3 kHz, 4 kHz, 6 kHz, and 8 kHz) and attenuator setting (e.g. 5-100 dB). For example, each CCA-100e Computer Controlled Audiometer, is preferably configured to generate an electrical output signal into a stable transducer load to a tolerance of ±0.3 dB. By keeping the output of each audiometer module 22 of a given model essentially the same, the only variation in the system output results from variations in conversion of the electrical output signal from audiometer module 22 to sound signals in transducers 24.

It will be appreciated that a variety of approaches may be employed within the scope of the present invention to enable test signal generator output level adjustment. Although a feedback amplifier is desirable for tightly controlling gain, an impedance network, or even a single resistor, may be connected in series with the output.

Initial standardization of each audiometer module 22 of a given model may be done by testing the output of each audiometer module 22 and storing initial calibration and correction factors in non-volatile data storage associated with audiometer module 22. CPU module 34 in each audiometer module 22 can then use those initial correction factors to control attenuators 26 to produce an electrical output signal of the desired uniform magnitude at each of the left signal output 30 and right signal output 32. Alternatively, components of audiometer module 22, in particular those in oscillator 26, attenuators 28 and final amplifier 29, may be selected so as to be within specified tolerances (i.e. ±2% and more preferably ≦±1%). This will ensure that each audiometer module 22 of a given model will produce output signals of a uniform magnitude within the acceptable range without the need for any initial correction factors. Parts and circuits can also be trimmed during manufacturing using adjustable value components (e.g. potentiometers, variable inductors, etc.) to ensure that each audiometer module 22 produces output signals having a uniform magnitude within the acceptable range.

Due to variation in gain, the sound output magnitude from transducers 24 of the same make and model for a given signal input magnitude will deviate, and further, the deviation may vary for signals of different frequencies. For example, industry standard TDH-39 transducers typically have an amplitude deviation of up to ±3 dB for the same input signal magnitude and frequency. The amount of deviation for each individual transducer 24 can be determined through acoustic calibration and testing. To determine the deviation, transducers 24 are connected to audiometer module 22 and the acoustic output of each transducer 24 measured on a sound level meter at each of a set of specified frequencies (e.g. 500 Hz, 1 kHz, 2 kHz, 3 kHz, 4 kHz, 6 kHz, and 8 kHz.). Because the audiometer module 22 output, and therefore the magnitude of the electronic signal input to the transducer, is standardized as set forth above and is therefore known, transducer correction values for each frequency to correct for the sound output deviation of each transducer 24 can then be determined directly from the meter readings for each transducer 24.

Figure 8:
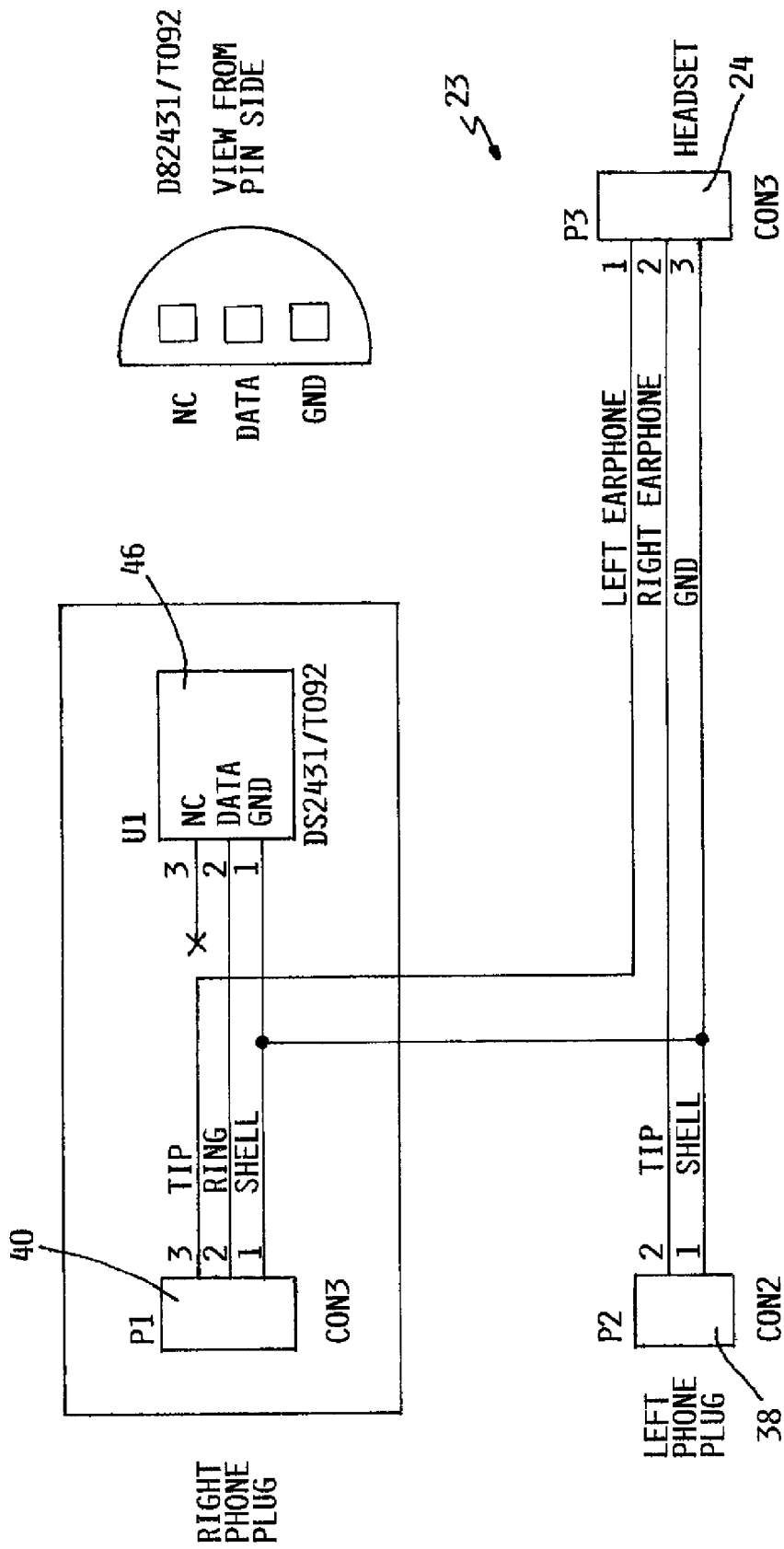
FIG. 8 is a block schematic diagram of a transducer according to an embodiment of the invention.

Once the transducer correction values for a transducer 24 have been determined, they can be stored electronically on a non-volatile memory chip 46 associated with transducer 24, such as, for example, an EEPROM chip, built into the transducer set 23 or its cabling. In an example embodiment depicted in schematic form in FIG. 8, a Dallas Semiconductor DS2431/TO92 EEPROM available from Newark In/One, Chicago, Ill., is built and wired into the right phone plug associated with transducer set 23. Those of skill in the art will appreciate that any other EEPROM or other non-volatile memory device may also be used, and any other structure for electronic interconnection of the non-volatile memory device may also be used while remaining within the scope of the present invention.

One wire interface controller 36, as depicted in schematic form in FIGS. 7A-7E, generally includes a protocol bridge device 47 to enable acquisition of the transducer correction values stored on non-volatile memory chip 46 and to transmit them to CPU module 34. In an exemplary embodiment, protocol bridge device 47 is a Dallas Semiconductor DS2482 I$^2$C to 1-Wire ®bridge device that interfaces directly to fast (400kHz max) I$^2$C master bus 49 coupled to CPU module 34. Firmware logic for the Intel 8051 microcontroller embodiment depicted in FIGS. 1-8 is disclosed in the Computer Program Listing Appendix and is fully incorporated by reference herein.

When transducer 24 is connected to audiometer module 22, the audiometer CPU module 34 reads the transducer correction values from non-volatile memory chip 46 via one-wire interface controller 36, and may store them in non-volatile memory in CPU module 34, such as EEPROM 60. CPU module 34 can interrogate the EEPROM before each test or from time to time to detect a change of transducers. When a test signal is subsequently generated by the oscillator 26, the CPU module 34 automatically adjusts the variable attenuators 28 based on the transducer correction values to adjust the magnitude of the signal output from audiometer module 22 to correct for the deviation of the particular transducer 24 being used. Thus, an audiometer module 22 can be used with any transducer 24, and need not be limited to use with only a certain transducer with which it was specifically calibrated.

In an alternative embodiment, the transducer correction values determined when calibrating the transducers 24 can be inscribed on a label or tag affixed to transducer 24. The date and type of the transducer 24 may also be included. When a transducer 24 is connected to an audiometer module 22, the user can enter the correction values into personal computer 54 via a suitable user interface screen. The personal computer 54 then communicates them to the audiometer CPU module 34 via interface 62, which may be a standard RS-232 serial connection. Logic for a calibration procedure for an example embodiment using a personal computer along with logic enabling a serial connection with audiometer module 22 is disclosed in the Computer Program Listing Appendix and is fully incorporated by reference herein.

CPU module 34 then automatically adjusts the variable attenuators 28 to correct for the deviation from the particular transducer 24 so that the signal output magnitude of audiometer module 22 results in the desired absolute sound signal output magnitude from transducer 24. In alternative embodiments wherein personal computer 54 is not used as an interface, a data input device such as a keyboard may be connected directly to CPU module 34 to input the correction values. It will be appreciated that in any of these embodiments, the transducer correction values may be combined with any initial correction values established and stored during output standardization of audiometer module 22. Those skilled in the art will also recognize that other alternative embodiments are possible, such as incorporating variation correcting electronics into the transducer assembly itself.

Transducer response typically varies over a range of a few dB. For example, the Telephonics TDH39 may vary plus or minus 3 dB at frequencies up to 6 kHz and more than that at 8 kHz. Applicable American National Standards Institute (ANSI) standards require that response be calibrated to within 3 dB or better. Because most modern audiometers are adjusted in discrete steps of 1 dB, those of skill in the art are accustomed to device calibration to within a fraction of a decibel, i.e. plus or minus 0.5 dB. Embodiments of the present invention will enable calibration within these or even closer tolerances. For instance, with a target tolerance of equal to or less than 0.5 dB, the present invention can enable test signal generator output variation of less than 0.1 dB, and transducer correction values in steps of 0.5 dB. This ensures that any combinations of test signal generator and transducers would vary by no more than 0.35 dB (0.1 plus half of 0.5 dB). Other combinations of tolerances for each component or the target tolerance itself are possible within the scope of the present invention. A tolerance of plus or minus 3 dB is desirable for most frequencies, and more desirable is less than 0.5 dB The embodiments above are intended to be illustrative and not limiting. Additional embodiments are encompassed within the scope of the claims. Although the present invention has been described with reference to particular embodiments, those skilled in the art will recognize that changes may be made in form and detail without departing from the spirit and scope of the invention. For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An audiometer for testing the hearing of a test subject, the audiometer comprising:

an audiometer module including a test signal generator and a processor with associated memory and control logic operably coupled to the test signal generator, wherein the processor controls the test signal generator to generate an electronic test signal having a first signal magnitude, wherein the processor further controls the test signal generator to adjust the first signal magnitude to a second signal magnitude in proportion to a transducer correction value and to deliver the electronic test signal with the second signal magnitude at an output of the audiometer module;

a transducer communicatively coupled to the output of the audiometer module, wherein the transducer generates a sound signal having a desired magnitude when the electronic test signal having the second signal magnitude is delivered to the transducer, wherein the transducer further comprises a data storage structure, and wherein the transducer correction value is stored by the data storage structure; and an interface selectively couplable with the processor for delivering the transducer correction factor to the processor.

2. The audiometer of claim 1, wherein the data storage structure is electronic memory.

3. The audiometer of claim 2, wherein the electronic memory is an EEPROM chip.

4. The audiometer of claim 1, wherein the data storage structure comprises printed indicia attached to the transducer.

5. The audiometer of claim 1, wherein the processor controls the test signal generator to generate a plurality of test signals, each of the test signals having a separate transducer correction value associated therewith, and wherein each of the separate transducer correction values is stored by the data storage structure.

6. The audiometer of claim 1, wherein the interface comprises a keyboard communicatively coupled to the processor.

7. The audiometer of claim 1, wherein the interface comprises a personal computer communicatively coupled to the processor.

8. The audiometer of claim 1, wherein the data storage structure is electronic memory and wherein the interface comprises a one-wire interface controller.

9. A method for calibrating an audiometer and a transducer, the audiometer including a test signal generator and a processor, wherein the processor controls the test signal generator to generate a plurality of electronic test signals each having a first signal magnitude, wherein the processor further controls the test signal generator to adjust the first signal magnitude of each test signal to a second signal magnitude in proportion to a corresponding transducer correction value and to deliver the test signals to an input of the transducer at the second signal magnitude, the method comprising:

applying each one of a plurality of input signals to the input of the transducer, each of the input signals having a signal frequency corresponding to a signal frequency of one of the test signals;

determining a target signal magnitude for each of the plurality of input signals that results in a desired magnitude of sound output from the transducer;

for each of the plurality of input signals, determining a transducer correction value for the audiometer that results in the corresponding test signal having a second signal magnitude equal to the target signal magnitude determined for the input signal;

storing the transducer correction values in a data storage structure associated with the transducer; and delivering the stored transducer correction values to the audiometer.

10. An audiometer for testing the hearing of a test subject, the audiometer comprising:

an audiometer module including means for generating a plurality of test signals, each test signal having a discrete frequency, and means for controlling the means for generating test signals, wherein the means for controlling includes means for adjusting each of the test signals to a predetermined magnitude according to a plurality of transducer correction values, each transducer correction value corresponding to one of the test signals;

a transducer for converting the test signals to sound signals communicatively coupled to the audiometer module, wherein when each test signal is delivered to the transducer at the predetermined magnitude, the transducer generates a sound signal having a desired signal magnitude, the transducer further including means for storing the transducer correction values in coded form; and means for communicating the transducer correction values stored in coded form to the means for controlling of the audiometer module.

11. The audiometer of claim 10, wherein the means for storing the transducer correction values includes electronic memory.

12. The audiometer of claim 11, wherein the electronic memory is an EEPROM chip.

13. The audiometer of claim 10, wherein the means for storing the transducer correction values comprises indicia attached to the transducer.

14. The audiometer of claim 10, wherein the means for communicating the transducer correction values includes a keyboard.

15. The audiometer of claim 10, wherein the means for communicating the transducer correction values includes a personal computer.

16. The audiometer of claim 10, wherein the means for storing the transducer correction values is electronic memory and wherein the means for communicating the transducer correction values includes a one-wire interface controller.

17. A method of calibrating an audiometer and transducer, the audiometer comprising a test signal generator and a processor controlling the test signal generator, the method comprising:

storing a plurality of transducer correction values in a data storage structure associated with the transducer;

retrieving the transducer correction values from the transducer using a controller associated with the audiometer and delivering the retrieved transducer correction values to the processor;

generating a test signal with the test signal generator; and using the processor to adjust a magnitude of the test signal according to at least one of the transducer correction values.

18. The method of claim 17, wherein the step of storing the plurality of correction values in a data storage structure associated with the transducer includes writing the correction values to an EEPROM.

19. The method of claim 17, wherein the step of storing the plurality of correction values in a data storage structure associated with the transducer includes inscribing the correction values on a label or tag.

20. The method of claim 17, further comprising determining the plurality of transducer correction values for the transducer using a sound level meter.

* * * * *